(12) United States Patent
Hillman et al.

(10) Patent No.: US 9,963,488 B2
(45) Date of Patent: May 8, 2018

(54) VARIANTS OF THE LANTIBIOTIC MU1140 AND OTHER LANTIBIOTICS WITH IMPROVED PHARMACOLOGICAL PROPERTIES AND STRUCTURAL FEATURES

(71) Applicants: Oragenics, Inc., Alachua, FL (US); The Texas A&M University System, College Station, TX (US)

(72) Inventors: Jeffrey D. Hillman, Gainesville, FL (US); James Leif Smith, College Station, TX (US); Shawanda R. Wilson-Stanford, College Station, TX (US)

(73) Assignees: Oragenics, Inc., Alachua, FL (US); The Texas A&M University System, College Station, TX (US)

( * ) Notice: Subject to any disclaimer, the term of this patent is extended or adjusted under 35 U.S.C. 154(b) by 0 days. days.

(21) Appl. No.: 14/381,420

(22) PCT Filed: Feb. 22, 2013

(86) PCT No.: PCT/US2013/027336
§ 371 (c)(1),
(2) Date: Aug. 27, 2014

(87) PCT Pub. No.: WO2013/130349
PCT Pub. Date: Sep. 6, 2013

(65) Prior Publication Data
US 2015/0125503 A1    May 7, 2015

Related U.S. Application Data

(60) Provisional application No. 61/603,693, filed on Feb. 27, 2012, provisional application No. 61/603,661, filed on Feb. 27, 2012.

(51) Int. Cl.
| | | |
|---|---|---|
| *C07K 14/195* | (2006.01) | |
| *A61K 39/09* | (2006.01) | |
| *C07K 14/315* | (2006.01) | |
| *A23G 4/12* | (2006.01) | |
| *A23L 2/52* | (2006.01) | |
| *A61K 8/99* | (2017.01) | |
| *A61K 35/744* | (2015.01) | |
| *A61Q 11/00* | (2006.01) | |
| *C12N 9/04* | (2006.01) | |
| *A01N 25/34* | (2006.01) | |
| *A01N 63/02* | (2006.01) | |
| *A61K 38/16* | (2006.01) | |
| *A61K 45/06* | (2006.01) | |
| *A61K 8/64* | (2006.01) | |
| *A61K 39/02* | (2006.01) | |
| *A61K 38/12* | (2006.01) | |

(52) U.S. Cl.
CPC ............ *C07K 14/195* (2013.01); *A01N 25/34* (2013.01); *A01N 63/02* (2013.01); *A23G 4/123* (2013.01); *A23L 2/52* (2013.01); *A61K 8/64* (2013.01); *A61K 8/99* (2013.01); *A61K 35/744* (2013.01); *A61K 38/164* (2013.01); *A61K 39/09* (2013.01); *A61K 45/06* (2013.01); *A61Q 11/00* (2013.01); *C07K 14/315* (2013.01); *C12N 9/0006* (2013.01); *A23V 2002/00* (2013.01); *A61K 38/12* (2013.01); *A61K 39/02* (2013.01); *A61K 2800/74* (2013.01); *C12Y 101/01001* (2013.01)

(58) Field of Classification Search
CPC ........ A01N 25/34; A01N 63/02; A23G 4/123; A23L 2/52; A23L 1/3014; A23L 33/135; A23V 2002/00; A61K 2800/74; A61K 35/744; A61K 38/12; A61K 38/164; A61K 39/09; A61K 45/06; A61K 8/64; A61K 8/99; A61K 39/02; A61Q 11/00; C07K 14/195; C07K 14/315; C12N 9/0006; C12Y 101/01001

See application file for complete search history.

(56) References Cited

U.S. PATENT DOCUMENTS

| 5,885,811 A | 3/1999 | Hansen |
|---|---|---|
| 6,391,285 B1 | 5/2002 | Hillman |

(Continued)

FOREIGN PATENT DOCUMENTS

| WO | 96/16180 A1 | 5/1996 |
|---|---|---|
| WO | 98/56411 | 12/1998 |

(Continued)

OTHER PUBLICATIONS

Smith et al., "Therapeutic Potential of Type A (I) Lantibiotics, a Group of Cationic Peptide Antibiotics", Curr Opin Microbial., 11(5):401-408 (2008).
Smith et al., "Covalent structure of mutacin 1140 and a novel method for the rapid identification of lantibiotics", Eur. J. Biochem. 267:6810-6816 (2000).
Ghobrial et al., "Pharmacodynamic activity of the lantibiotic MU1140", Int J. Antimicrob Agents, 33(1):70-74 (2009).
Wilson-Stanford et al., "Oxidation of Lanthionines Renders the Lantibiotic Nisin Inactive", Applied and Environmental Microbiology, 75(5):1381-1387 (2009).

(Continued)

Primary Examiner — Marcela M Cordero Garcia
(74) Attorney, Agent, or Firm — McDonnell Boehnen Hulbert & Berghoff LLP

(57) ABSTRACT

The invention provides improvements of lantibiotics useful for reducing the numbers of microbes or the reproduction of microbes in or on subjects or objects. One embodiment of the invention provides variants of antibiotics wherein the amino acid at position (1) is changed to Ile or Gly, the amino acid at position (4) is changed to an Ala, the amino acid at position (4) is removed, the amino acid at position (5) is changed to an Ala, or wherein, as in the case of MU1140, the amino acid at position (13) is Arg, the Arg at position (13) is substituted with Asp, or combinations of two or more these changes or a pharmaceutically acceptable salt thereof.

20 Claims, 8 Drawing Sheets

(56) References Cited

U.S. PATENT DOCUMENTS

| | | |
|---|---|---|
| 2002/0128186 A1 | 9/2002 | Hillman |
| 2006/0198793 A1 | 9/2006 | Hillman |
| 2009/0068121 A1 | 3/2009 | O'Sullivan et al. |
| 2009/0215985 A1 | 8/2009 | Kirichenko |
| 2009/0304783 A1 | 12/2009 | Walsh |

FOREIGN PATENT DOCUMENTS

| | | |
|---|---|---|
| WO | 08/151434 | 12/2008 |
| WO | 09/135945 | 11/2009 |
| WO | 10/117652 A1 | 10/2010 |

OTHER PUBLICATIONS

International Search Report for corresponding PCT application No. US2013/027336, dated Jun. 12, 2013.

Smith et al., "Structure and Dynamics of the Lantibiotic Mutacin 1140", Biochemistry, 42:10372-10384 (2003).

Chatterjee et al., "Biosynthesis and Mode of Action of Lantibiotics", Chem. Rev., 105:633-683 (2005).

Ghobrial et al., "Pharmacokinetic and Pharmacodynamic Evaluation of the Lantibiotic MU1140", Journal of Pharmaceutical Sciences, 99(5):2521 (2010).

Hasper et al., "An Alternative Bactericidal Mechanism of Action for Lantibiotic Peptides that Target Lipid II", Science, 313:1636 (2006).

Smith et al., "Elucidation of the Antimicrobial Mechanism of Mutacin 1140", Biochemistry, 47:3308-3314 (2008).

Ross et al., "Fundamental functionality: recent developments in understanding the structure-activity relationships of antibiotic peptides", The Journal of Antibiotics, 64:27-34 (2011).

Bierbaum et al., "Lantibiotics: Mode of Action, Biosynthesis and Bioengineering", Current Pharmaceutical Biotechnology, 10:2-18 (2009).

Lubelski et al., "Biosynthesis, immunity, regulation, mode of action and engineering of the model lantibiotic nisin", Cell. Mol. Life Scl, 65:455-476 (2008).

Chan et al., "Structure-Activity Relationships in Peptide Antibiotic Nisin: Role of Dehydroalanine 5", Applied and Environmental Microbiology, 62(8):2966-2969 (1996).

UniProt database No. Q2QBT0 dated Mar. 18, 2008.

Geneseq database No. AEK39859 dated Nov. 2, 2006.

EMBL database No. AR210490 dated Jun. 21, 2002.

EMBL database No. FW557628 dated Dec. 29, 2010.

Geneseq database No. AAV72289 dated May 25, 1999.

EMBL database No. AR243257 dated Dec. 21, 2002.

EBI accession No. AXQ88364 dated Nov. 12, 2009.

Piper et al., "Bioengineering of a Nisin A-producing Lactococcus lactis to create isogenic strains producing the natural variants Nisin F, Q and Z", Microbial Biotechnology, 4(3):375-382 (2010).

European Search Report for corresponding European Patent application No. 137553533, dated Nov. 10, 2015.

EBI accession No. AUP72648 dated Feb. 19, 2009.

EBI accession No. AUP72847 dated Feb. 19, 2009.

Wild-type (native) MU1140

Schematic of Variations to MU1140

Abbreviations and symbols: ins = insertion and Δ = deletion.

Figure 2: Primers Used for Mutagenesis of MU1140

| Oligonucleotide | Sequence (5' – 3') |
|---|---|
| SRWlanA_1 | A<u>GAATTC</u>AGGATGCTATCGCTGCTTTTTTTGTG (SEQ ID NO:1) |
| SRWlanA_2 | A<u>GAATTC</u>AGGAAAGTTGCCATATGGTTTTGTG (SEQ ID NO:2) |
| Phe1Gly_1 | GATCCAGATACTCGTGGCAAAAGTTGGAGCCTTTGTACG (SEQ ID NO:27) |
| Phe1Gly_2 | CAACTTTTGCCACGAGTATCTGGATCGTCGTTGC (SEQ ID NO:28) |
| Phe1Ile_1 | GATCCAGATACTCGTATCAAAAGTTGGAGCCTTTGTACG (SEQ ID NO:29) |
| Phe1Ile_2 | CAACTTTTGATACGAGTATCTGGATCGTCGTTGC (SEQ ID NO:30) |
| Trp4Ala_1 | GCAAGCCTTTGTACGCCTGGTTG (SEQ ID NO:3) |
| Trp4Ala_2 | ACAAAGGCTTGCACTTTTGAAACG (SEQ ID NO:4) |
| Trp4insAla_1 | GCAAGCCTTTGTACGCCTGGTTG (SEQ ID NO:5) |
| Trp4insAla_2 | CAAAGGCTTGCCCAACTTTTGAAACG (SEQ ID NO:6) |
| ΔTrp4_1 | ---AGCCTTTGTACGCCTGGTTG (SEQ ID NO:7) |
| ΔTrp4_2 | CGTACAAAGGCTACTTTTGAAACG (SEQ ID NO:8) |
| Dha5Ala_1 | GCACTTTGTACGCCTGGTTGTGC (SEQ ID NO:9) |
| Dha5Ala_2 | GGCGTACAAAGTGCCCAACTTTTGAA (SEQ ID NO:10) |
| Ala7insAla_1 | GCAACGCCTGGTTGTGCAAGGAC (SEQ ID NO:11) |
| Ala7insAla_2 | ACCAGGCGTTGCACAAAGGCTCC (SEQ ID NO:12) |
| Arg13Asp_1 | GACACAGGTAGTTTCAATAGTTAC (SEQ ID NO:13) |
| Arg13Asp_2 | GAAACTACCTGTGTCTGCACAACCAG (SEQ ID NO:14) |
| Outside primers are SRWlanA_1 and SRWlanA_2 and are homologous to the 5' and 3' flanking DNA. Underlined section represents the engineered EcoRI site. Mutations are either bolded or dashes. Numbering designates forward (1) and reverse (2) for primers. | |

Alignment of mutants to Wild-type Sequence

```
Wild-type      TTCAAAAGTTGG---AGCCTTTGT---ACGCCTGGTTGTGCAAGGACAGGTAGTTTCAATAGTTACTGTTGC
Phe1Gly        GGCAAAAGTTGG---AGCCTTTGT---ACGCCTGGTTGTGCAAGGACAGGTAGTTTCAATAGTTACTGTTGC
Phe1Ile        ATCAAAAGTTGG---AGCCTTTGT---ACGCCTGGTTGTGCAAGGACAGGTAGTTTCAATAGTTACTGTTGC
Trp4Ala        TTCAAAAGTGCA---AGCCTTTGT---ACGCCTGGTTGTGCAAGGACAGGTAGTTTCAATAGTTACTGTTGC
Trp4insAla     TTCAAAAGTTGGGCAAGCCTTTGT---ACGCCTGGTTGTGCAAGGACAGGTAGTTTCAATAGTTACTGTTGC
ΔTrp4          TTCAAAAGT------AGCCTTTGT---ACGCCTGGTTGTGCAAGGACAGGTAGTTTCAATAGTTACTGTTGC
Ser5Ala        TTCAAAAGTTGG---GCACTTTGT---ACGCCTGGTTGTGCAAGGACAGGTAGTTTCAATAGTTACTGTTGC
Cys7insAla     TTCAAAAGTTGG---AGCCTTTGTGCAACGCCTGGTTGTGCAAGGACAGGTAGTTTCAATAGTTACTGTTGC
Arg13Asp       TTCAAAAGTTGG---AGCCTTTGT---ACGCCTGGTTGTGCAGACACAGGTAGTTTCAATAGTTACTGTTGC Wild-type      SEQ ID NO:15
Phe1Gly        SEQ ID NO:25
Phe1Ile        SEQ ID NO:26
Trp4Ala        SEQ ID NO:19
Trp4insAla     SEQ ID NO:20
ΔTrp4          SEQ ID NO:21
Ser5Ala        SEQ ID NO:22
Cys7insAla     SEQ ID NO:23
Arg13Asp       SEQ ID NO:24
```

Figure 3

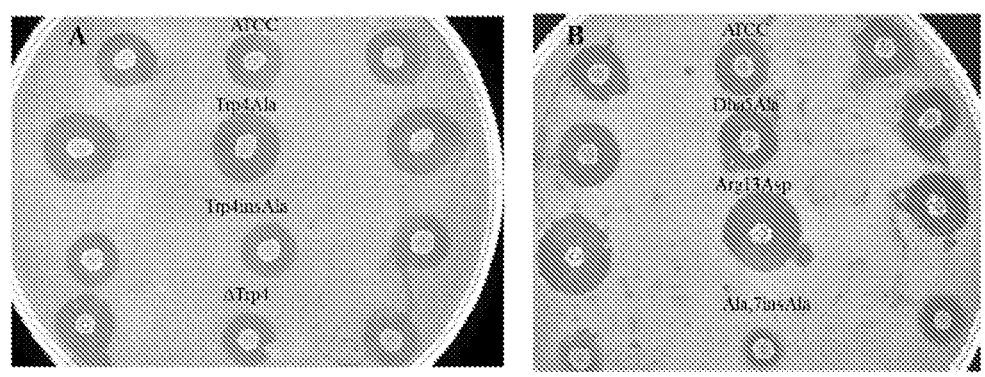
Figure 4A-B: Zone of Inhibition Plate Assays

Bioactivity of Strains Producing Variants of MU1140 Compared to Wild-Type MU1140

| Variant Produced | Mean Area* (mm$^2$) | Standard Error of the Mean (SEM) | Ratio of Variant to Wild-Type Activities | Statistical Significance (p value)[#] |
|---|---|---|---|---|
| MU1140 (wild-type) | 204.44 | 8.90 | - | - |
| Phe1Gly | 321.85 | 46.52 | 1.57 | <.001 |
| Phe1Ile | 372.78 | 75.90 | 1.82 | <.001 |
| Trp4Ala | 434.80 | 46.10 | 2.12 | <.001 |
| Trp4insAla | 212.37 | 24.70 | 1.04 | >.05 |
| ∇Trp4 | 217.56 | 35.37 | 1.06 | >.05 |
| Dha5Ala | 382.25 | 31.40 | 1.87 | <.001 |
| Ala$_s$7insAla | 109.41 | 9.74 | 0.54 | <.001 |
| Arg13Asp | 526.06 | 55.09 | 2.57 | <.001 |

* Based on 10 independent samples.
[#] Student's t Test

Nisin A (Q)(Z)(F)(U)
Ile-Dhb-Ala$_s$-Ile-Dha-Leu-sAla-Abu$_s$-Pro-Gly-$_s$Ala-Lys-Abu$_s$-Gly-
Ala(Val)(Ala)(Ala)(Ile)-Leu-Met-Gly(Gly)(Gly)(Gly)(Dhb)-$_s$Ala-
Asn(Asn)(Asn)(Asn)(Pro)-Met(Lue)(Met)(Met)(Leu)-Lys-Abu$_s$-Ala-Abu$_s$-$_s$Ala-
His(Asn)(Asn)(Asn)(Gly)-$_s$Ala-Ser(Ser)(Ser)(Ser)(His)-Ile(Val)(Ile)(Val)(Phe)-
His(His)(His)(His)(Gly)-Val-Dha-Lys
*Nisin U doesn't have C-terminal Val Dha Lys   Nisin A (Q) SEQ ID NO:31; Nisin A
(Z) SEQ ID NO:32; Nisin A(F) SEQ ID NO:33; Nisin A(U) SEQ ID NO:34.*

Streptin
Val-Gly- Ala$_s$-Arg-Tyr-Leu-$_s$Ala-Abu$_s$-Pro-Gly-Ala$_s$-$_s$Ala-Trp-Lys-Leu-Val-$_s$Ala-Phe-Dhb-
Dhb-Dhb-Val-Lys   (SEQ ID NO:35)

Ericin A
Val-Leu- Ala$_s$-Lys-Dha-Leu-$_s$Ala-Abu$_s$-Pro-Gly-$_s$Ala-Ile-Abu$_s$-Gly-Pro-Leu-Gln-Abu$_s$-$_s$Ala-
Trp-Leu-$_s$Ala-Phe-Pro-Abu$_s$-Phe-Ala-Lys-$_s$Ala (SEQ ID NO:36)

Ericin S
Trp-Lys-Ala$_s$-Glu-Dha-Val-$_s$Ala-Abu$_s$-Pro-Gly-$_s$Ala-Val-Abu$_s$-Gly-Val-Leu-Gln-Abu$_s$-$_s$Ala-
Phe-Leu-Gln-Dhb-Ile-Abu$_s$-$_s$Ala-Asn-$_s$Ala-His-Ile-Dha-Lys (SEQ ID NO:37)

Subtilin
Trp-Lys-Ala$_s$-Glu-Dha-Leu-$_s$Ala-Abus-Pro-Gly-$_s$Ala-Val-Abu$_s$-Gly-Ala-Leu-Gln-Dhb-
$_s$Ala-Phe-Leu-Gln-Abu$_s$-Ala-Asn-$_s$Ala-Lys-Ile-Dha-Lys (SEQ ID NO:38)

Epidermin ([Val1-Leu6]-epidermin) (Gallidermin)
Ile (Val)(Ile)-Ala-Ala$_s$-Lys-Phe-Ile (Leu) (Ile)-$_s$Ala-Abu$_s$-Pro-Gly-$_s$Ala-Ala-
Lys-Dhb-Gly-Ala$_s$-Phe-Asn-Ala$_s$-Tyr-$_s$Ala-NHCHCH (SEQ ID NO:39)
*Staphylococcin 1580 is the same as epidermin.
Staphylococcin T is the same as Gallidermin.*

Mutacin III (B-NY266)
Phe-Lys-Ala$_s$-Trp-Dha-Leu (Phe)-$_s$Ala-Abu$_s$-Pro-Gly-$_s$Ala-Ala-Arg(Lys)-Dhb-Gly-
Ala$_s$-Phe-Asn-Ala$_s$-Tyr-$_s$Ala-NHCHCH (SEQ ID NO:40)
*Mutacin III has the same sequence as MU1140.*

Mutacin I
Phe-Dha-Ala$_s$-Leu-Dha-Leu-$_s$Ala-Ala$_s$-Leu-Gly-$_s$Ala-Thr-Gly-Val-Lys-Asn-Pro-Ala$_s$-
Phe-Asn-Ala$_s$-Tyr-$_s$Ala-NHCHCH SEQ ID NO:41

Microbisporicin A1 (A2)
Val-Dhb-Ala$_s$-ClTrp-Dha-Leu-$_s$Ala-Abu$_s$-Pro-Gly-$_s$Ala-Thr-Ala$_s$-3,4-diOHPro (4-OHPro)-
Gly-Gly-Gly-Ala$_s$-Asn-$_s$Ala-Ala$_s$-Phe-$_s$Ala-NHCHCH   SEQ ID NO:42

Clausin
Phe-Dhb-Ala$_s$-Val-Dha-Phe-$_s$Ala-Abu$_s$-Pro-Gly-$_s$Ala-Gly-Glu-Dhb-Gly-Ala$_s$-Phe-Asn-Ala$_s$-
Phe-$_s$Ala-NHCHCH   SEQ ID NO:43

Abbreviations:   ClTrp: 5-chloro-Trp, OHPro: hydroxylated Pro, NHCHCH: AviCys

Positions of amino acid modifications similar to mutacin 1140 are underlined.
Alternate amino acids are in parenthesis.

VARIANTS OF THE LANTIBIOTIC MU1140 AND OTHER LANTIBIOTICS WITH IMPROVED PHARMACOLOGICAL PROPERTIES AND STRUCTURAL FEATURES

PRIORITY

This application claims the benefit of U.S. provisional application 61/603,661, filed Feb. 27, 2012, and U.S. provisional application 61/603,693, filed Feb. 27, 2012, which are both incorporated herein by reference in their entirety.

SEQUENCE LISTING

This document incorporates by reference an electronic sequence listing text file, which was electronically submitted along with this document. The text file is named 11-1115-WO-US_ST25.txt, is 20.8 kilobytes, and was created on Apr. 27, 2017.

BACKGROUND OF THE INVENTION

Many strains of medically important bacteria have become increasingly resistant to currently available antibiotics. Healthcare associated infections caused by multi-drug resistant pathogens are particularly vexing. Worldwide, millions suffer from antibiotic-resistant infections, which results in a huge cost to the healthcare system. The need for new antibiotics has become a critical, unmet need in the medical community (Infectious Diseases Society of America, 2010).

Lantibiotics, an important class of antibiotics with potential clinical relevance (reviewed in Smith & Hillman, (2008) Curr. Opin. Microbiol. 11:401), acquired their name because of the characteristic lanthionine rings that are present. Lantibiotics are also known to have various unusual amino acids such as 2,3-didehydroalanine (Dha), 2,3-didehydrobutyrine (Dhb), S-amino vinyl-D-cysteine (AviCys), aminobutyrate (Abu), 2-oxopropionyl, 2-oxobutyryl, and hydroxypropionyl. Hasper et al. (2006) Science 313, 1636-1637. Mutacin 1140 ("MU1140") rings A and B (see FIG. 1A), the lipid II binding domain, is similar to nisin, a well-known lantibiotic produced by $Lactococcus~lactis$ that has been used in the food industry for over 50 years. It was discovered that both nisin and MU1140 abduct lipid II from the site of new cell wall synthesis, ultimately causing cell death. Smith et al. (2008) Biochemistry 47:3308-3314.

Particular features of lantibiotics, such as their novel and diverse mechanisms of action and, in instances where it has been studied (Chatterjee et al., (2005) Chem Rev. 105:633), the difficulty of sensitive bacteria to acquire resistance, have aroused considerable interest in these molecules as potential therapeutic agents. Until now, organic synthesis of lantibiotics also has been thwarted because of the complex intertwined ring structures found in these highly unusual peptide molecules (e.g., Rings C/D of MU1140 in FIG. 1A).

The problem of synthesizing intertwined macrocyclic rings characteristic of lantibiotics has recently been solved. See, U.S. Pat. No. 7,521,529; U.S. Publ. No. 2009/0215985. Differentially Protected Orthogonal Lanthionine Technology (DPOLT) is a peptide synthesis platform technology that has excellent potential for the cost-effective, large scale manufacture of all known lantibiotics. The crux of DPOLT involves manufacture of two novel, differentially protected lanthionine (Alanine-S-Alanine) building blocks for intertwined ring construction. The use of these building blocks, in combination with standard solid and/or solution phase peptide synthesis chemistry, is essential for synthesis of the intertwined rings.

MU1140 can be synthesized by a particular strain of the oral microorganism $Streptococcus~mutans$. Smith et al. (2000) Eur. J. Biochem. 267:6810-6816. When laboriously produced through large scale fermentation methods and purified using stepwise precipitation, chromatographic, and crystallization methods, it demonstrated a submicromolar minimum inhibitory concentration (MIC) for all Gram positive bacteria against which it was tested. Ghobrial et al. (2009) International Journal of Antimicrobial Agents 33:70-74. The study also demonstrated that MU1140 is bactericidal against $S.~pneumonia$ and multi-drug resistant strains of $S.~aureus$, bacteriostatic against vancomycin-resistant $Enterococcus~faecium$ (VREF), and had no activity against Gram-negative bacteria or yeast. See id. The study showed that MU1140's time-kill profiles for selected pathogens were similar to those of vancomycin, one of the currently used antibiotics of last resort. See id. It has a novel mechanism of action which involves binding to and abducting lipid II essential for cell wall biosynthesis. Hasper et al., (2006) Science, 313:1636; Smith et al., (2008) Biochem. 47:3308. It had low cytotoxicity in vitro, low toxicity when administered via an intravenous route in murine models, and it was distributed into all body compartments. Ghobrial et al., J. Pharm. Sci. Epub: Dec. 28, 2009, DOI 10.1002/jps.22015. Demonstration of efficacy was achieved in a pilot study in which 60 times the $LD_{50}$ of $Staphylococcus~aureus$ was administered in a rat peritonitis model. Development of significant resistance was not observed during repeated subculture of $S.~aureus$ or $Streptococcus~pneumoniae$ in medium containing sub-lethal concentrations of MU1140. Ghobrial et al. (2009) International Journal of Antimicrobial Agents 33:70-74. The basis for this observation may be due, in part, to the fact that the molecular target, lipid II, is evolutionarily ancient and highly conserved throughout the bacterial kingdom, indicating that mutations which alter its structure and/or function may be prohibited. The molecular structure of MU1140 contains four macrocyclic rings (see FIG. 1A), each of which contains a lanthionine or methyl-lanthionine residue. This odd chemical feature is likely to be important in the resistance of MU1140 to hydrolytic degradation, as has been reported. Hillman et al., Infect. Immun. 44:141 (1984). Resistance to hydrolysis may also be, in part, a reflection of the unusual, horseshoe-shaped three dimensional structure of MU1140. Smith et al. (2003) Biochem. 42:10372-10384. Based on these and other studies, MU1140 has the potential to replace current, failing drugs of last resort and serve in the treatment of problematic infections caused by Gram positive bacteria such as methicillin resistant $S.~aureus$ (MRSA), vancomycin resistant $Enterococci$ (VRE), and $Clostridium~difficile$ (C. diff).

SUMMARY OF THE INVENTION

One embodiment of the invention provides variants of lantibiotics wherein the amino acid at position 1 is changed to Ile or Gly, the amino acid at position 4 is changed to an Ala, the amino acid at position 4 is removed, the amino acid at position 5 is changed to an Ala, or wherein, as in the case of MU1140, the amino acid at position 13 is Arg, the Arg at position 13 is substituted with Asp, or combinations of two or more these changes or a pharmaceutically acceptable salt thereof. The variant lantibiotic can additionally have one or more Lys residues at positions 12, 13, 14, 15, 22, 23, 27, or 32 substituted with an Asp. Besides MU1140, variant lantibiotics include, for example, nisin, epidermin, epidermin [Val1 and Leu6], gallidermin, staphylococcin 1580, staphylococcin T, mutacin B-NY266, mutacin III, mutacin I, microbisporicin A1 and microbisporicin A2, clausin, streptin, ericin A, ericin S, subtilin, or a pharmaceutically acceptable salt thereof.

The variant lantibiotic can be, for example, (a) nisin wherein the Ile at position 1 is changed to Gly, the Ile at position 4 is changed to an Ala or is removed; the Dha at position 5 is changed to an Ala, the Lys at position 12 is changed to an Asp, the Lys at position 22 is changed to an Asp, or combinations thereof;

(b) epidermin, epidermin [Val1 and Leu6], gallidermin, staphylococcin 1580 or staphylococcin T wherein the Ile or Val at position 1 is changed to Ile or Gly, the Lys at position 4 is changed to an Ala or is removed, the Phe at position 5 is changed to an Ala, the Lys at position 13 is changed to an Asp, or combinations thereof;

(c) mutacin B-NY266 wherein the Phe at position 1 is changed to Ile or Gly, the Trp at position 4 is changed to an Ala or is removed, the Dha at position 5 is changed to an Ala, the Lys at position 13 is changed to an Asp, or combinations thereof;

(d) mutacin III wherein the Phe at position 1 is changed to Ile or Gly, the Trp at position 4 is changed to an Ala or is removed, the Dha at position 5 is changed to an Ala, the Arg at position 13 is changed to an Asp, or combinations thereof;

(e) mutacin I wherein the Phe at position 1 is changed to Ile or Gly, the Leu at position 4 is changed to an Ala or is removed, Dha at position 5 is changed to an Ala, the Lys at position 15 is changed to an Asp, or combinations thereof;

(f) microbisporicin A1 and microbisporicin A2 wherein the Trp at position 1 is changed to Ile or Gly, the Cloro-Trp at position 4 is changed to an Ala or is removed, the Dha at position 5 is changed to an Ala, or combinations thereof;

(g) clausin wherein the Phe at position 1 is changed to Ile or Gly, the Val at position 4 is changed to an Ala or is removed, the Dha at position 5 is changed to an Ala, or combinations thereof;

(h) streptin wherein the Trp at position 1 is changed to Ile or Gly, the Arg at position 4 is changed to an Ala or is removed, the Tyr at position 5 is changed to an Ala, the Lys at position 14 is changed to an Asp, the Lys at position 23 is changed to an Asp, or combinations thereof;

(i) ericin A wherein the Val at position 1 is changed to Ile or Gly, the Lys at position 4 is changed to an Ala or is removed, the Dha at position 5 is changed to an Ala, the Lys at position 28 is changed to an Asp, or combinations thereof;

(j) ericin S wherein the Trp at position 1 is changed to Ile or Gly, the Glu at position 4 is changed to an Ala or is removed, the Dha at position 5 is changed to an Ala, the Lys at position 32 is changed to an Asp, or combinations thereof; or (k) subtilin wherein the Trp at position 1 is changed to Ile or Gly, the Glu at position 4 is changed to an Ala or is removed, the Dha at position 5 is changed to an Ala, the Lys at position 27 is changed to an Asp, the Lys at position 30 is changed to an Asp, or combinations thereof;

or a pharmaceutically acceptable salt thereof.

Another embodiment of the invention provides variants of the lantibiotic MU1140 comprising Formula I:

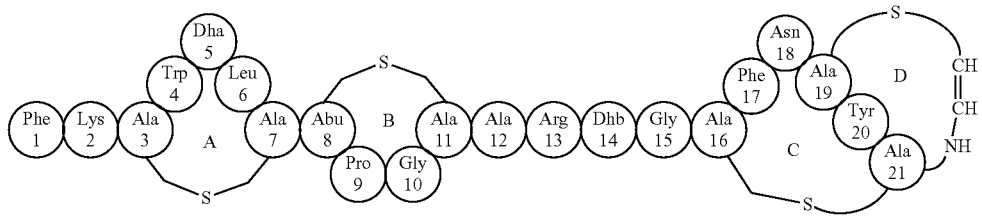

(SEQ ID NO:17), wherein the following amino acid substitutions are present: Phe1Ile or Phe1Gly; Trp4Ala; Dha5Ala; Arg13Asp; or combinations thereof, or a pharmaceutically acceptable salt thereof. The variant lantibiotic can further comprise a Trp4insAla mutation or a ΔTrp4 mutation. The following amino acid substitutions can also be present: Abu8Ala, or Dhb14Ala, or both Abu8Ala and Dhb14Ala. The vinyl group of ring D (—CH=CH—) can be an ethyl group (—CH$_2$—CH$_2$—).

Another embodiment of the invention provides an antimicrobial composition comprising one or more isolated variant lantibiotics of the invention and a pharmaceutically acceptable carrier, pharmaceutically acceptable diluent, other diluent or excipient. The composition can further comprise at least one antifungal agent, one additional antimicrobial agent, a membrane disrupting agent, or combinations thereof. The one additional antimicrobial agent can have Gram negative bacteriostatic or bacteriocidal activity and the membrane disrupting agent can render Gram negative bacteria susceptible to the variant lantibiotic. The one or more isolated lantibiotics can be present in the composition at about 0.001, 0.01, 0.1, 1, 5, 10, 20, 30, 40, 50, 75, 100, 200, 300, 400, 500, 600, 700, 800, 900, 1,000 or more mg/kg or mg/L.

Still another embodiment of the invention provides a method of reducing reproduction of bacteria or reducing numbers of bacteria present in or on a subject, comprising administering to the subject a therapeutically effective amount of an antimicrobial composition of the invention. The subject can be a human or animal. The composition can be administered orally or topically, nasally, buccally, sublingually, transmucosally, rectally, transdermally, by inhalation, by injection or intrathecally. The injection can be intramuscular, intravenous, intrapulmonary, intramuscular, intradermal, intraperitoneal, intrathecal, or subcutaneous injection.

Yet another embodiment of the invention comprises a preservative comprising an effective amount of one or more variant lantibiotics of the invention in a physiological solution at a pH of between 3 and 8.

Even another embodiment of the invention provides a food, beverage, gum, or dentifrice composition comprising an amount of one or more variant lantibiotics of the invention sufficient to reduce the reproduction of bacteria or numbers of bacteria in the food, beverage, gum or dentifrice composition.

Another embodiment of the invention provides a method of reducing reproduction of bacteria or reducing numbers of bacteria present in or on a composition or object to be treated, comprising contacting an antimicrobial composition of the invention with the composition or object to be treated for a period effective to reduce reproduction of bacteria or reduce numbers of bacteria in or on the composition or object. The composition to be treated can be, e.g., a food, beverage, gum, or dentifrice.

Yet another embodiment of the invention provides a purified polynucleotide comprising SEQ ID NOs: 19-26 or combinations thereof.

Even another embodiment of the invention provides a composition comprising a solid surface or a woven or non-woven textile with a variant lantibiotic composition of the invention coated onto, immobilized, linked, or bound to the solid surface or textile.

Another embodiment of the invention provides a method of reducing a biofilm or biofouling condition comprising contacting an antimicrobial composition of the invention with the biofilm or biofouling condition for a period effective to reduce reproduction of bacteria or reduce numbers of bacteria in or on the biofilm or biofouling condition.

Yet another embodiment of the invention provides a kit comprising one or more lantibiotic mutacins of the invention and one or more applicators.

Therefore, the invention provides, inter alia, unique variants of the lantibiotic MU1140 and other lantibiotics with improved pharmacological properties and methods of using the compositions to treat and prevent infections, diseases, and colonizations by one or more types of bacteria.

BRIEF DESCRIPTION OF THE DRAWINGS

FIG. 2 shows the primers used for mutagenesis of MU1140.

FIG. 3 shows the BLAST sequence of chromosomal DNA highlighting the introduced mutations of the variant MU1140 lanA polynucleotide sequences with the wild type MU1140 lanA polynucleotide sequence.

FIG. 4A-B shows the results of the zone of inhibition plate assays.

FIG. 5 shows the means and standard deviations for the bioactivity of strains producing variants of MU1140 compared to wild-type MU1140.

FIG. 7 shows the sequence of lantibiotics having structural similarity to MU1140. Amino acid substitutions in naturally occurring variants of lantibiotics (e.g., nisin A, nisin Q, nisin C, nisin F, and nisin U) are shown in parentheses in the same order as the listed variants.

DETAILED DESCRIPTION OF THE INVENTION

Figure 1A:
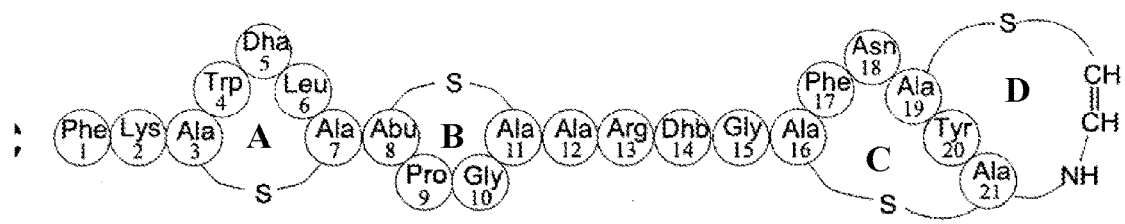
FIG. 1A shows the primary amino acid sequence and macrocyclic rings of wild-type MU1140 (SEQ ID NO:17).

As used herein, the singular forms "a," "an," and "the" include plural referents unless the context clearly dictates otherwise.

MU1140 has an overall horseshoe-like shape kinked at the "hinge region" between rings B and C. Smith et al. (2003) Biochem. 42:10372-10384. This shape is the result of a turn-like motif in the hinge region that folds the amino-terminal AB rings (the lipid II binding domain) towards the carboxy-terminal overlapped rings CD. The flexibility of the hinge region is believed to be important in promoting lateral assembly of MU1140, enabling it to abduct and sequester lipid II. The ψ angle of Trp4 and φ angle of Dha5 in ring A help contribute to its flexibility. Also it was determined that the ψ bond of $_S$Ala7 (a residue that is not confined by the thioether ring) rotates 360° allowing ring A to spin freely with respect to ring B. This flexibility is thought to be important in orienting rings A and B during lipid II binding. The hinge region also contains a potentially enzymatically susceptible arginine at residue 13. Mutations in the structural gene (lanA) for MU1140 were generated to determine the effect of the following amino acid alterations: Phe1Ile, Phe1Gly, Trp4Ala, Trp4insAla, ΔTrp4, Dha5Ala, Ala$_S$7insAla, and Arg13Asp. FIG. 1B.

It was found that the variants of MU1140 possessing a deletion of Trp4 or insertion of Ala after Trp4 showed bioactivity activity approximately equivalent to the wild-type in a deferred antagonism assay using *Micrococcus luteus* strain ATCC 272 as the target strain. Wilson-Sanford et al., (2009) Appl. Environ. Microbiol. 75:1381. In this assay, activity is determined by calculating the area of the zone of inhibition. These results indicate that shortening or lengthening ring A had no deleterious effect on MU1140 activity, indicating an unexpected permissiveness in the structure of ring A. As shown in FIG. 5, the Trp4Ala substitution resulted in a statistically significant (p<0.001) increase in bioactivity when compared to the wild-type. Since both amino acids are uncharged and hydrophobic, it can be speculated that the difference in bioactivity was due to the size difference between the two amino acids. Replacement of Dha5 with Ala also resulted in a statistically significant (p<0.001) increase in bioactivity. This mutation is potentially very useful since solid phase synthesis will be simplified by incorporation of Ala in place of Dha, and should therefore impact on cost of goods. Insertion of alanine after $_S$Ala at position 7 resulted in a significant (p<0.001) reduction of bioactivity. While not wishing to be bound to any particular theory, since it has been determined that $_S$Ala7 freely rotates 360° allowing ring A to spin freely with respect to ring B, it could be concluded that the Ala$_S$7insAla mutation changed the orientation of the rings during lipid II binding, possibly affecting the affinity of the molecule for its substrate, lipid II. The Arg13Asp substitution showed a significant (p<0.001) increase in bioactivity when compared to the wild-type. While not wishing to be bound to any particular theory, the observed effect may be the result of increased solubility. This site-directed change has the potential to significantly improve MU1140 by decreasing the dose size and decreasing the possibility of hydrolysis.

As shown in FIG. 5, both the Phe1Ile and the Phe1Gly substitutions resulted in statistically significant (p<0.001)

increases in bioactivity when compared to the wild-type. While not wishing to be bound to any particular theory, the basis for the increase may be due to increased binding affinity to the lipid II target or to improved efficiency in cleavage of the leader sequence. It is noteworthy that substitution of Arg (AGA/AGG/CGT/CGC/CGA/CGG) with Asp (GAT/GAC) or the substitution of Ala (GCT/GCT/GCA/GCG) for Trp (TGG) or the substitution of Ala (GCT/GCT/GCA/GCG) for Ser (AGT/AGC) or the substitution of Ile (ATT/ATG) or Gly (GGT/GGC/CCA/GGG) for Phe (TTT/TTC) are all very unlikely to occur in nature since they involve multiple point mutations, which may include one or more transversions in the affected codon.

Variants of the Lantibiotic MU1140 and Other Lantibiotics with Improved Properties and Structural Features Variants of the lantibiotic MU1140 and other lantibiotics of the invention are polypeptides comprising post-translational modifications. Post-translational modifications are chemical modifications of a polypeptide after it has been translated. A polypeptide is a polymer of two or more amino acids covalently linked by amide bonds. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

Figure 1B:
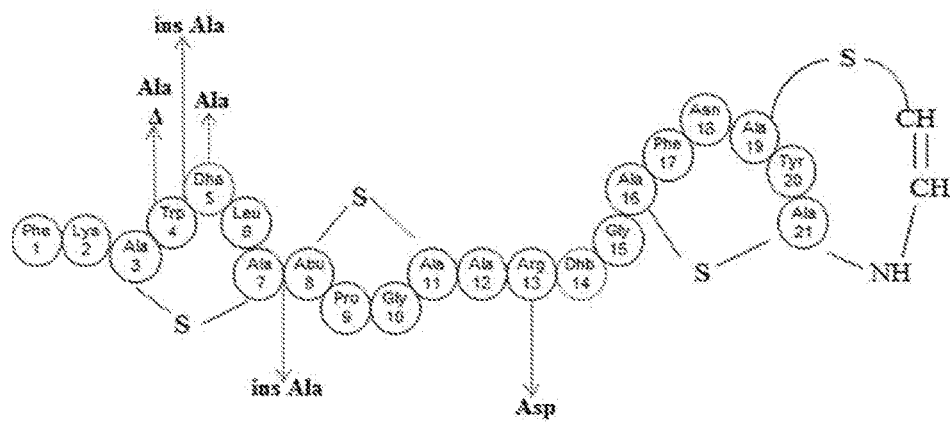
FIG. 1B shows amino acid substitution sites of MU1140 (SEQ ID NO:16) as described in this specification.

Wild-type MU1140 is shown in FIG. 1A. MU1140 has four rings labeled A, B, C, and D. Two of these rings are formed by lanthionine (Ala-S-Ala) residues, including one in Ring A ($Ala_3$-S-$Ala_7$) and one in Ring C ($Ala_{16}$-S-$Ala_{21}$); there is a methyl-lanthionine residue (Abu-S-Ala) that forms Ring B comprised of the α-aminobutyrate residue in position 8 and the Ala in position 11 ($Abu_8$-S-$Ala_{11}$); and the fourth ring, D, is comprised of the Ala in position 19 linked to an aminovinyl group by a thioether linkage ($Ala_{19}$-S—CH=CH—NH—).

One embodiment of the invention provides one or more of the following variants of the lantibiotic mutacin, MU1140, shown in FIG. 1B (SEQ ID NO:16). That is, the invention includes variants of the wild-type lantibiotic MU1140 (SEQ ID NO:17) with one or more of the following mutations:

1. Phe1Ile or Phe1Gly; that is the phenylalanine at position 1 is changed to isoleucine or glycine;
2. Trp4Ala; that is, the tryptophan at position 4 is changed to alanine.
3. Dha5Ala; that is, the 2,3-didehydroalanine at position 5 is changed to alanine;
4. Arg13Asp; that is, the arginine at position 13 is changed to aspartate.

In one embodiment of the invention a variant of the lantibiotic MU1140 comprises a Phe1Ile or Phe1Gly amino acid substitution; a Trp4Ala amino acid substitution; a Dha5Ala amino acid substitution; an Arg13Asp amino acid substitution; or combinations thereof. An MU1140 variant of the invention can also comprise, e.g., a Trp4insAla in which an alanine is inserted after the fourth tryptophan residue; or a ΔTrp4 in which there is a deletion of the tryptophan at position 4. Other amino acid changes can be present. For example, the following amino acid substitutions can be present: $Abu_S8Ala_S$, or Dhb14Ala, or both Abu8Ala and Dhb14Ala. Furthermore, the vinyl group of ring D (—CH=CH—) can be an ethyl group (—$CH_2$—$CH_2$—). These changes may improve the pharmacological properties of the lantibiotic mutacins of the invention. These changes will also make the molecules easier and less expensive to synthesize. Where the $Abu_S8Ala_S$ substitution is present, ring B of the lantibiotic mutacin will be a lanthionine bridge instead of a methyllanthionine bridge.

Biologically active equivalents of lantibiotic polypeptides can have one or more conservative amino acid variations or other minor modifications and retain biological activity. A biologically active equivalent has substantially equivalent function when compared to the corresponding lantibiotic, e.g., MU1140. In one embodiment of the invention a lantibiotic has about 1, 2, 3, 4, or 5 or less conservative amino acid substitutions.

Similar mutations and amino acid substitutions can be made in other lantibiotics with similar structures to MU1140 (see FIG. 7) resulting in variant lantibiotics with advantageous properties and structural features. A variant lantibiotic has one or more amino acid mutations, substitutions, deletions or additions as compared to the wild-type lantibiotic. The term "lantibiotics of the invention" includes all variant lantibiotics described herein. For example, amino acid substitutions and deletions can occur in nisin at analogous positions (Ile1, Ile4, Dha5 and Lys22) and in epidermin, gallidermin and staphylococcin (Ile1 or Val1, Lys4, Phe5, and Lys13).

That is, the Ile at position 1 of nisin can be changed to a Gly, the Ile at position 4 can be changed to an Ala or deleted; the Dha at position 5 can be changed to an Ala, the Lys at position 12 can be changed to an Asp, the Lys at position 22 can be changed to an Asp, or combinations thereof.

For epidermin, epidermin [Val1 and Leu6], gallidermin, staphylococcin 1580, or staphylococcin T, the Ile or Val at position 1 can be changed to Ile or Gly, the Lys at position 4 can be changed to an Ala or removed, the Phe at position 5 can be changed to an Ala, the Lys at position 13 can be changed to an Asp, or combinations thereof.

For mutacin B-NY266 the Phe at position 1 can be changed to Ile or Gly, the Trp at position 4 can be changed to an Ala or removed, the Dha at position 5 can be changed to an Ala, the Lys at position 13 can be changed to an Asp, or combinations thereof.

For mutacin III the Phe at position 1 can be changed to Ile or Gly, the Trp at position 4 can be changed to an Ala or removed, the Dha at position 5 can be changed to an Ala, the Arg at position 13 can be changed to an Asp, or a combination thereof. For mutacin I the Phe at position 1 can be changed to Ile or Gly, the Leu at position 4 can be changed to an Ala or removed, the Dha at position 5 can be changed to an Ala, the Lys at position 15 can be changed to an Asp, or combinations thereof.

For microbisporicin A1 and microbisporicin A2 the Val at position 1 can be changed to Ile or Gly, the Cloro-Trp at position 4 can be changed to an Ala or removed, the Dha at position 5 can be changed to an Ala, or combinations thereof.

For clausin the Phe at position 1 can be changed to Ile or Gly, the Val at position 4 can be changed to an Ala or can be removed, the Dha at position 5 can be changed to an Ala, or combinations thereof.

For streptin the Trp at position 1 can be changed to Ile or Gly, the Arg at position 4 can be changed to an Ala or can be removed, the Tyr at position 5 can be changed to an Ala, the Lys at position 14 can be changed to an Asp, the Lys at position 23 can be changed to an Asp, or combinations thereof.

For ericin A the Val at position 1 can be changed to Ile or Gly, the Lys at position 4 can be changed to an Ala or removed, the Dha at position 5 can be changed to an Ala, the Lys at position 28 can be changed to an Asp, or combinations thereof.

For ericin S the Trp at position 1 can be changed to Ile or Gly, the Glu at position 4 can be changed to an Ala or removed, the Dha at position 5 can be changed to an Ala, the Lys at position 32 can be changed to an Asp, or combinations thereof.

For subtilin the Trp at position 1 can be changed to Ile or Gly, the Glu at position 4 can be changed to an Ala or removed, the Dha at position 5 can be changed to an Ala, the Lys at position 27 can be changed to an Asp, the Lys at position 30 can be changed to an Asp, or combinations thereof.

Biologically active equivalent lantibiotic mutacins or other lantibiotic polypeptides can generally be identified by modifying one of the variant lantibiotic sequences of the invention, and evaluating the properties of the modified antibiotic to determine if it is a biological equivalent. A lantibiotic is a biological equivalent if it reacts substantially the same as a lantibiotic of the invention in an assay such as a zone of inhibition assay, e.g. has 90-110% of the activity of the original lantibiotic.

A conservative substitution is one in which an amino acid is substituted for another amino acid that has similar properties, such that one skilled in the art of peptide chemistry would expect the secondary structure and general nature of the polypeptide to be substantially unchanged. In general, the following groups of amino acids represent conservative changes: (1) ala, pro, gly, glu, asp, gln, asn, dha, abu, dhb, ser, thr; (2) cys, ser, tyr, thr; (3) val, ile, leu, met, ala, gly, dha, abu, dhb, phe; (4) lys, arg, his; and (5) phe, tyr, trp, his.

A lantibiotic of the invention can be covalently or non-covalently linked to an amino acid sequence to which the lantibiotic is not normally associated with in nature, i.e., a heterologous amino acid sequence. A heterologous amino acid sequence can be from a non-*Streptococcus mutans* organism, a synthetic sequence, or an *S. mutans* sequence not usually located at the carboxy or amino terminus of a lantibiotic of the invention. Additionally, a lantibiotic of the invention can be covalently or non-covalently linked to compounds or molecules other than amino acids such as indicator reagents. A lantibiotic of the invention can be covalently or non-covalently linked to an amino acid spacer, an amino acid linker, a signal sequence, a stop transfer sequence, TMR stop transfer sequence, a transmembrane domain, a protein purification ligand, or a combination thereof. A polypeptide can also be linked to a moiety (i.e., a functional group that can be a polypeptide or other compound) that facilitates purification (e.g., affinity tags such as a six-histidine tag, trpE, glutathione-S-transferase, maltose binding protein, staphylococcal Protein A or com), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more amino acid residues at, for example, the amino terminus or carboxy terminus of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a lantibiotic of the invention can be part of a fusion protein, which can contain heterologous amino acid sequences. Heterologous amino acid sequences can be present at the C or N terminus of a lantibiotic of the invention to form a fusion protein. More than one lantibiotic of the invention can be present in a fusion protein. Fragments of lantibiotics of the invention can be present in a fusion protein of the invention. A fusion protein of the invention can comprise one or more lantibiotic of the invention, fragments thereof, or combinations thereof.

Pharmaceutically acceptable salts, esters, amides, and prodrugs are carboxylate salts, amino acid addition salts, esters, amides, and prodrugs of the lantibiotic mutacins are part of the present invention. These compounds are suitable for use with subjects and do not cause undue toxicity, irritation, or allergic response, are commensurate with a reasonable benefit/risk ratio, and are effective for their intended use. Salts are the substantially non-toxic, inorganic and organic acid addition salts of lantibiotics of the invention. Salts include, for example, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like.

Pharmaceutically acceptable, non-toxic esters of lantibiotics of the invention include, for example, $C_1$-$C_6$ alkyl esters wherein the alkyl group is a straight or branched chain. Other esters include $C_5$-$C_7$ cycloalkyl esters as well as arylalkyl esters such as, but not limited to benzyl $C_1$-$C_4$ alkyl esters.

Pharmaceutically acceptable, non-toxic amides of lantibiotics of the invention include amides derived from ammonia, primary $C_1$-$C_6$ alkyl amines and secondary $C_1$-$C_6$ dialkyl amines wherein the alkyl groups are straight or branched chains. In the case of secondary amines, the amine may be in the form of a 5- or 6-membered heterocycle containing one nitrogen atom. Also included are amides derived from ammonia, $C_1$-$C_3$ alkyl primary amines, and $C_1$-$C_2$ dialkyl secondary amines.

In one embodiment of the invention a lantibiotic polypeptide of the invention can be synthesized using DPOLT methodologies. See e.g., U.S. Pat. No. 7,521,529; U.S. Publ. No. 2009/0215985. A lantibiotic of the invention can be produced recombinantly. A polynucleotide encoding a lantibiotic of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. A lantibiotic of the invention can also be purified from *S. mutans* cell culture.

Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide.

The polynucleotides of the invention encode the polypeptides of the invention described above (see FIGS. 1 and 7). In one embodiment of the invention the polynucleotides encode a polypeptide shown in SEQ ID NOs:19-26 (see FIG. 3), combinations thereof, or fragments thereof.

Polynucleotides of the invention can consist of less than about 66, 60, 50, 45, 30, 15 (or any range between about 66 and 15) contiguous nucleotides. The purified polynucleotides can comprise additional heterologous polynucleotides (that is, nucleotides that are not from *Streptococcus mutans*) and even additional *Streptococcus mutans* polynucleotides. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and *Staphylococcal* protein A. One embodiment of the invention provides a purified polynucleotide comprising at least about 6, 10, 15, 20, 25, 30, 40, 45, 50, 60, 66, or more contiguous nucleotides of encoding SEQ ID NOs:19-26.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length. Isolated polynucleotides also include non-naturally occurring nucleic acid molecules. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 95, 96, 97, 98, or 99% identical to the polynucleotide sequences of the invention and the complements thereof are also polynucleotides of the invention. Degenerate nucleotide sequences are polynucleotides that encode a polypeptide of the invention or fragments thereof, but differ in nucleic acid sequence from the given polynucleotide sequence, due to the degeneracy of the genetic code.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al. (1984) *Nuc. Acids Res.* 12:387), BLASTP, BLASTN, FASTA (Atschul et al. (1990) *J. Molec. Biol.* 215:403), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman ((1981) *Adv. App. Math.*, 2:482-489). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Polynucleotides of the invention can be isolated from nucleic acid sequences present in, for example, a bacterial sample. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Compositions

The lantibiotics of the invention can act as antimicrobials, disinfectants, antibiotics, antiseptics, preservatives, antiviral or decontaminating agents. An antimicrobial composition kills microbes or slows the reproduction of microbes such as bacteria. A disinfectant composition is applied to a non-living object to kill microbes or to slow the reproduction of microbes such as bacteria. An antibiotic kills microbes or slows the reproduction of microbes, such as bacteria, in the body of a subject or in cells or tissues. An antiseptic kills microbes or slows the reproduction of microbes, such as bacteria, on skin, tissue or organs. A preservative composition kills microbes or slows the reproduction of microbes in products such as paints, wood, foods, beverages, biological samples, cell or tissue cultures or pharmaceutical compositions to prevent decomposition by microbes such as bacteria. A decontaminating agent is a cleaning agent that can be used to kill microbes or to reduce the reproduction of microbes, such as bacteria, in or on a living organism, cells, tissues, or objects.

The lantibiotics of the invention can be bacteriostatic, meaning that the lantibiotics reduce or prevent the reproduction of bacteria. In one embodiment of the invention the bacteriostatic action of a variant MU1140 lantibiotic reduces reproduction of the bacteria by about 5, 10, 20, 30, 40, 50, 60, 70, 80, 90, or 100% (or any range between about 5% and 100%). The lantibiotics of the invention can be bacteriocidal, meaning that the lantibiotics kill bacteria. In one embodiment of the invention the variant MU1140 lantibiotics kill about 5, 10, 20, 30, 40, 50, 60, 70, 80, 90, or 100% (or any range between about 5% and 100%) of the bacteria they come in contact with. The difference between whether a lantibiotic acts as bacteriostatic agent or a bacteriocidal agent can be the amount or concentration of lantibiotic delivered to the subject, composition, or object to be treated. Lantibiotics of the invention can reduce the numbers of bacteria present in a composition, subject, cells, or tissues to be treated. In one embodiment of the invention, variant MU1140 lantibiotics reduce the number of bacteria by about 5, 10, 20, 30, 40, 50, 60, 70, 80, 90, or 100% (or any range between about 5% and 100%).

The isolated variant lantibiotics of the invention can be present in antimicrobial compositions comprising one or more isolated lantibiotics of the invention and one or more pharmaceutically acceptable carriers, diluents or excipients (solids or liquids). In one embodiment of the invention, the variant lantibiotic is present in an amount effective to substantially reduce bacterial reproduction of at least one type of Gram-positive bacteria by about 5, 10, 20, 30, 40, 50, 60, 70, 80, 90 or 100% (or any range between about 5 and 100%). In one embodiment of the invention the variant MU1140 lantibiotic is present in an amount effective to substantially reduce the numbers of at least one type of Gram-positive bacteria by about 5, 10, 20, 30, 40, 50, 60, 70, 80, 90 or 100% (or any range between about 5 and 100%). The at least one type of Gram-positive bacteria can be, for example, *Staphylococcus aureus*, methicillin resistant *Staphylococcus aureus*, *Staphylococcus saprophyticus*, *Staphylococcus epidermidis*, vancomycin resistant *Enterococci*, vancomycin resistant *Enterococcus faecalis*, *Enterococcus faecalis*, *Enterococcus faecium*, *Propionibacterium acnes*, *Streptococcus salivarius*, *Streptococcus sanguis*, *Streptococcus mitis*, *Streptococcus pyogenes*, *Lactobacillus salivarius*, *Listeria monocytogenes*, *Actinomyces israelii*, *Actinomyces naeslundii*, *Actinomyces viscosus*, *Bacillus anthracis*, *Streptococcus agalactiae*, *Streptococcus intermedius*, *Streptococcus pneumoniae*, *Corynebacterium diphtheria*, *Clostridium sporogenes Clostridium botulinum*, *Clostridium perfringens*, *Clostridium tetani*, and *Clostridium difficile*. All Gram positive species tested are susceptible to lantibiotic mutacins of the invention.

Furthermore, Gram negative bacteria can be susceptible to lantibiotic mutacins of the invention where the outer membrane is disrupted with, for example, a chelating agent such as Tris, Tris-EDTA, or EDTA. Any membrane disrupting compounds can be added to compositions of the invention to increase the sensitivity of Gram negative bacteria to the lantibiotic mutacins of the invention, for example, polymixins, membrane disrupting antibiotics, cecropins (e.g., *Musca domestica* cecropin, hyalophora cecropins, cecropin B, cecropin P1), G10KHc (see Eckert et al., (2006) Antimicrob. Agents Chemother. 50:1480); alpha and beta defensins, ovine derived cathelicidine (see Anderson et al., (2004) Antimicrob. Agents Chemother. 48:673), squalamine derivatives (e.g., SM-7, see Kikuchi et al., (1997) Antimicrob. Agents Chemother. 41:1433, sodium hexametaphosphate, cellular enzymes of granulocytes (van den Broek, (1989) Rev. Infect. Dis. 11:213), EM49 (Rosenthal et al., (1976) Biochemistry, 15:5783), and sodium lauryl sarcosinate. The combination of lantibiotic mutacins of the invention with a membrane disruption agent and/or other antibiotics or drugs that target Gram negative species can provide a composition effective against both Gram positive and Gram negative species. Therefore, the invention includes compositions comprising one or more lantibiotics of the invention and at least one additional antimicrobial agent or membrane disrupting agent. The one or more additional antimicrobial agents can have Gram negative bacteriostatic or bacteriocidal activity. The membrane disrupting agent can render Gram negative bacteria susceptible to a lantibiotic of the invention (i.e., the membrane disrupting agent in combination with one or more lantibiotic mutacins of the invention are bacteriostatic or bacteriocidal to Gram negative bacteria). Gram negative bacteria include, for example, *Bordatella pertussis*, *Borrelia burgdorferi*, *Brucella abortus*, *Brucella canis*, *Brucella melitensis*, *Brucella suis*, *Campylobacter jejuni*, *Escherichia coli*, *Francisella tularensis*, *Haemophilus influenza*, *Helicobacter pylori*, *Legionella pneumophila*, *Leptospira interrogans*, *Neisseria gonorrhoeae*, *Neisseria meningitides*, *Pseudomonas aeruginosa*, *Rickettsia rickettsii*, *Salmonella typhi*, *Salmonella typhimurium*, *Shigella sonnei*, *Treponema pallidum*, *Vibrio cholera*, and *Yersinia pestis*.

Gram variable and Gram indeterminate bacteria can also be susceptible to lantibiotic mutacins of the invention. Chelating agents such as EDTA can be added to compositions of the invention to disrupt the outer membrane of these organisms. Gram variable and Gram indeterminate bacteria include, for example, *Chlamydia pneumoniae*, *Chlamydia trachomatis*, *Chlamydia psittaci*, *Mycobacterium leprae*, *Mycobacterium tuberculosis*, *Mycobacterium ulcerans*, and *Mycoplasma pneumoniae*.

A lantibiotic of the invention can be combined with one or more pharmaceutically acceptable carriers, other carriers, diluents, adjuvants, excipients or encapsulating substances, which are suitable for administration to an animal, composition, or object. Exemplary pharmaceutically acceptable carriers, other carriers, diluents, adjuvants, excipients or encapsulating substances thereof include sugars, such as lactose, glucose, dextrose, and sucrose; starches, such as corn starch and potato starch; cellulose and its derivatives, such as sodium carboxymethyl cellulose, ethyl cellulose, hydropropylmethylcellulose, and methyl cellulose; polysaccharides such as latex functionalized SEPHAROSE® and agarose; powdered tragacanth; glycerol; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, propylene glycol, and polyethylene glycol; proteins such as serum albumins, keyhole limpet hemocyanin, immunoglobulin molecules, thyroglobulin, ovalbumin, tetanus toxoid; alginic acid; emulsifiers, such as the TWEEN® s (polysorbate); polylactic acids; polyglycolic acids; polymeric amino acids such as polyglutamic acid, and polylysine; amino acid copolymers; peptoids; lipitoids; inactive avirulent virus particles or bacterial cells; liposomes; hydrogels; cyclodextrins; biodegradable nanocapsules; bioadhesives; wetting agents, such sodium lauryl sulfate; coloring agents; flavoring agents; tableting agents; stabilizers; antioxidants; preservatives; pyrogen-free water; isotonic saline; ethanol; ethyl oleate; pyrrolidone; Ringer's solution, dextrose solution, Hank's solution; sodium alginate; polyvinylpyrrolidone; gum tragacanth; gum acacia; and sterile water and aqueous buffers and solutions such as physiological phosphate-buffered saline.

Carriers, such as pharmaceutically acceptable carriers and diluents, for therapeutic use are well known in the art and are described in, for example, Remington's Pharmaceutical Sciences, Mack Publishing Co. (A. R. Gennaro ed. (1985)).

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates.

The variant lantibiotic compositions can be in a form suitable for oral use, for example, as tablets, troches, lozenges, mouthwashes, dentifrices, buccal tablets, solutions, aqueous or oily suspensions, dispersible powders or granules, emulsions, hard or soft capsules, or syrups or elixirs. Such compositions can contain one or more agents, such as emulsifying agents, wetting agents, pH buffering agents, sweetening agents, flavoring agents, coloring agents and preserving agents. The lantibiotic compositions can be a dry product for reconstitution with water or other suitable liquid before use.

Lantibiotic of the invention can also be administered in the form of suppositories for rectal, vaginal, or urethral administration of the drug. These compositions can be prepared by mixing the variant lantibiotic with a suitable non-irritating carrier that is solid at ordinary temperatures but liquid at the body temperature and will therefore melt in the rectum to release the drug. Such materials are cocoa butter and polyethylene glycols.

A lantibiotic of the invention can also be topically administered in the form of, e.g., lotions, gels, or liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other dosage forms include, for example, injectable, sublingual, and nasal dosage forms. Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Formulations can contain between about 0.0001% and about 99.9999% by weight of one or more lantibiotic of the invention and usually at least about 5, 10, 15, 20, 25, 30, 40, 50, 60, 70, 80, 90, or 100% (weight %) of one or more lantibiotic mutacins of the present invention. Some embodiments contain from about 25% to about 50% or from 5% to 75% of a lantibiotic of invention.

One or more lantibiotics of the invention can be combined with one or more antimicrobials, antibiotics, bacteriocins, anti-viral, virucidal, or anti-fungal compounds or molecules to form a composition useful in the methods of the invention. Antibiotics include, for example, penicillins, cephalosporins, polymixins, quinolones, sulfonamides, aminoglycosides, macrolides, tetracyclines, cyclic lipopeptides (e.g., daptomycin), glycylcyclines (e.g., tigecycline), and oxazolidinones (e.g., linezoid).

Bacteriocins include, for example, acidocin, actagardine, agrocin, alveicin, aureocin, carnocin, carnocyclin, colicin, curvaticin, divercin, duramycin, enterocin, enterolysin, epidermin, erwiniocin, gallidermin, glycinecin, halocin, haloduracin, lactococin, lacticin, leucoccin, macedocin, mersacidin, mesentericin, microbisporicin, mutacin, nisin, paenibacillin, planosporicin, pediocin, pentocin, plantaricin, reutericin, sakacin, salivaricin, subtilin, sulfolobicin, thuricin 17, trifolitoxin, variacin, vibriocin, warnericin, and warnerin.

Antifungals include, for example, polyene antifungals (e.g., amphotericin B, natamycin, rimocidin, filipin, nystatin, candicin, hamycin), azole antifungals (e.g., imidazole, triazole, thiazole), imidazoles (e.g., miconazole, ketoconazole, clotrimazole, econazole, omoconazole, bifonazole, butoconazole, fenticonazole, isoconazole, oxiconazole, sertaconazole, sulconazole, tioconazole), triazoles (e.g., fluconazole, itraconazole, isavuconazole, ravuconazole, posaconazole, voriconazole, terconazole, albaconazole), thiazoles (e.g., abagungin), allylamines (e.g., terbinafine, naftifine, butenafine), echinocandins (e.g., anidulafungin, caspofungin, micafungin), polygodial, benzoic acid, ciclopiroxolamine, tolnaftate, undecylenic acid, flucytosine, and griseofulvin.

Antivirals and virucidal agents include, for example, abacavir, aciclovire, acyclovir, adefovir, amantadine, amprenavir, ampligen, arbidol, atazanavir, atripla, boceprevir, cidofovir, combivir, delavirdine, didanosine, docosanol, efavirenz, emtricitabine, enfuvirtide, entecavir, entry inhibitors, famciclovir, fomivirsen, fosamprenavir, foscarnet, fosfonet, ganciclovir, ibacitabine, imunovir, idoxuridine, imiquimod, indinavir, inosine, integrase inhibitor, interferon types i, ii, or iii, interferon, lamivudine, lopinavir, loviride, maraviroc, moroxydine, methisazone, nelfinavir, nevirapine, nexavir, nucleoside analogues, oseltamivir, peginterferon alpha-2a, penciclovir, peramivir, pleconaril, podophyllotoxin, protease inhibitor, raltegravir, reverse transcriptase inhibitor, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Use of Lantibiotics of the Invention

Lantibiotic compositions of the invention can be used to reduce the growth of bacteria, prevent the growth of bacteria, prevent the reproduction of bacteria, reduce the reproduction of bacteria, or to reduce or eliminate the numbers of bacteria present in or on an object, composition or subject. In one embodiment of the invention, the bacteria are at least one type of Gram positive bacteria, at least one type of Gram negative bacteria, at least one type of Gram variable or Gram indeterminate bacteria, or a combination of at least one type of Gram positive or at least one type of Gram negative bacteria or at least one type of Gram variable or Gram indeterminate bacteria. The lantibiotic compositions of the invention can be administered to, added to, or contacted with a composition or subject in need of treatment.

Lantibiotics of the invention can be used to treat, ameliorate, or prevent a disease, infection, or colonization. A disease is a pathological condition of a part, organ, or system of an organism resulting from infection and characterized by an identifiable group of signs and symptoms. An infection is invasion by and multiplication of pathogenic microorganisms, such as bacteria, in a bodily part or tissue, which may produce a subsequent tissue injury and progress to overt disease through a variety of cellular or toxic mechanisms. Colonization is the act or process of a microorganism, such as bacteria, establishing itself on or within a host or object. Colonization may produce a subsequent biofilm or biofouling condition as described below. Lantibiotics of the invention can be used prophylactically to prevent disease, infection or colonization or to prevent the spread of a disease, infection or colonization to additional bodily parts or tissues, additional surfaces, or to different subjects. Lantibiotics of the invention can also be used to reduce the number of pathogenic microorganisms on or in a subject or on a surface.

Examples of diseases, infections and colonizations that can be treated or prevented by the compositions and methods of the invention include, for example, septicemia, bacterial meningitis, cystic fibrosis, bovine mastitis, impetigo, bacterial vaginosis, bacterial pneumonia, urinary tract infections, bacterial gastroenteritis, erysipelas, cellulitis, anthrax, whooping cough, brucellosis, enteritis, opportunistic infections, community acquired respiratory infections, upper and lower respiratory infections, diphtheria, nosocomial infections, diarrhea, ulcer, bronchitis, listeriosis, tuberculosis, gonorrhea, pseudomonas infections, salmonellosis, shigellosis, staphylococcal infections, streptococcal infections, and necrotizing fasciitis.

Lantibiotics of the invention can be administered to a mammal, such as a mouse, rabbit, guinea pig, macaque, baboon, chimpanzee, human, cow, sheep, pig, horse, dog, cat, or to a non-mammalian animal such as a chicken, duck, or fish. Lantibiotics of the invention can also be administered to plants.

Administration of the lantibiotics of the invention can be by any means known in the art, including injection (e.g., intramuscular, intravenous, intrapulmonary, intramuscular, intradermal, intraperitoneal, intrathecal, or subcutaneous injection), aerosol, intranasal, infusion pump, suppository (rectal, vaginal, urethral), mucosally, topically, buccally, orally, parenterally, infusion techniques, by inhalation or spray, sublingually, transdermally, as an ophthalmic solution, intraspinal application, or by other means, in dosage unit formulations containing conventional non-toxic pharmaceutically acceptable carriers, diluents, excipients, adjuvants, and vehicles. A combination of administration methods can also be used.

In therapeutic applications, the lantibiotic compositions of the invention are administered to subjects to reduce the reproduction of bacteria or reduce the numbers of bacteria, or both. The particular dosages of lantibiotic in a composition will depend on many factors including, but not limited to the species, age, gender, severity of infection, concurrent medication, general condition of the animal to which the composition is administered, and the mode of administration of the composition. An effective amount of the composition of the invention can be readily determined using only routine experimentation. A therapeutically effective amount means the administration of that amount to an individual, either in a single dose or as part of a series, which is effective for treatment, amelioration, or prevention of bacterial infection or colonization. A therapeutically effective amount is also an amount effective in alleviating or reducing the symptoms of an infection or in reducing the reproduction of bacteria in or on a subject or reducing the amount of bacteria in or on a subject.

The concentration of lantibiotic in a composition can vary widely, and will be selected primarily based on activity of the lantibiotic, body weight of the subject, overall health of the subject, etc. as described above, in accordance with the particular mode of administration selected and the subject's needs. Concentrations, however, will typically be selected to provide dosages ranging from about 0.001, 0.01, 0.1, 1, 5, 10, 20, 30, 40, 50, 75, 100, 150 mg/kg/day (or any range between about 0.001 and 150 mg/kg/day) and sometimes higher. Typical dosages range from about 0.1 mg/kg/day to about 5 mg/kg/day, from about 0.1 mg/kg/day to about 10 mg/kg/day, from about 0.1 mg/kg/day to about 20 mg/kg/day, and from about 0.1 mg/kg/day to about 50 mg/kg/day.

Lantibiotics of the invention can be administered for a certain period of time (e.g., 1 day, 3 days, 1 week, 1 month, 2 months, 3 months, 6 months, 1 year or more) or can be administered in maintenance doses for long periods of time to prevent or reduce disease, infection, colonization, biofilms or biofouling conditions.

Lantibiotics of the invention can be administered either to an animal that is not infected or colonized with bacteria or can be administered to bacterially infected or colonized animal.

One embodiment of the invention provides a method for decontaminating or reducing bacterial growth on or in an inanimate object comprising contacting the object with a lantibiotic of the invention for a period effective to substantially inhibit bacterial growth of at least one type of bacteria. The contacting can be for 1, 15, 30, or 60 minutes, or 2, 3, 10, 12, 24, 36 or 48 hours (or any range between about 1 minute and 48 hours). An object can be, for example, a food preparation surface, food preparation equipment, industrial equipment, pipes, or a medical device such as catheter, scalpel, knife, scissors, spatula, expander, clip, tweezers, speculum, retractor, suture, surgical mesh, chisel, drill, level, rasp, saw, splint, caliper, clamp, forceps, hook, lancet, needle, cannula, curette, depressor, dilator, elevator, articulator, extractor, probe, staple, artificial joint, wound dressing, catheter, stent, tubing, bowl, tray, sponge, snare, spoon, syringe, pacemaker, screw, plate, pin, wire, guide wire, pacemaker lead, implant, sensor, glucose sensor, blood bypass tubing, i.v. bag, ventricular assist device components, ophthalmic lens, and balloon.

Other objects that can be decontaminated include textiles such as a woven (woven from natural or non-natural materials or a blend of natural and synthetic materials) or nonwoven material (e.g., elastic or non-elastic thermoplastic polymers). The textiles can be used for, e.g., a protective article worn by patients, healthcare workers, or other persons who may come in contact with potentially infectious agents or microbes, such as a gown, robe, face mask, head cover, shoe cover, or glove. Other protective textiles can include surgical drapes, surgical covers, drapes, sheets, bedclothes or linens, padding, gauze dressing, wipe, sponge and other antimicrobial articles for household, institutional, health care and industrial applications.

In one embodiment of the invention, a lantibiotic is coated onto, immobilized, linked, or bound to a solid surface such as a food preparation surface, food preparation equipment, industrial equipment, pipes, or a medical device such as catheter, scalpel, knife, scissors, spatula, expander, clip, tweezers, speculum, retractor, suture, surgical mesh, chisel, drill, level, rasp, saw, splint, caliper, clamp, forceps, hook, lancet, needle, cannula, curette, depressor, dilator, elevator, articulator, extractor, probe, staple, artificial joint, wound dressing, catheter, stent, tubing, bowl, tray, sponge, snare, spoon, syringe, pacemaker, screw, plate, pin, wire, guide wire, pacemaker lead, implant, sensor, glucose sensor, blood bypass tubing, i.v. bag, ventricular assist device components, ophthalmic lens, balloon and textiles as described above.

In another embodiment of the invention, lantibiotic compositions of the invention are present in a transdermal formulation. A transdermal formulation can be designed so the lantibiotic composition acts locally at the point of administration or systemically by entering an animal or human's blood circulation. Therefore, delivery can occur by direct topical application of the lantibiotic composition in the form of an ointment or lotion, or by adhesion of a patch embedded with the lantibiotic composition or with a reservoir that holds the lantibiotic composition and releases it to the skin all at once or in a time-controlled fashion.

Optionally, lantibiotic compositions can be contained within vesicles such as microparticles, microspheres, liposomes, lipid vesicles, or transfersomes for transdermal or topical delivery. Ultrasound devices to generate shock waves to enlarge pores, use of electric current to drive substances across skin, and the use of microneedles to pierce skin and deliver lantibiotic compositions into the bloodstream can also be used with transdermal or topical administration.

Methods of coating, binding, or immobilizing peptides, such as the lantibiotics of the invention onto surfaces are well-known in the art. See e.g., Modern Methods of Protein Immobilization, William H. Scouten, First Ed. (2001) CRC Press; Protein Immobilization (Biotechnology and Bioprocessing), Richard F. Taylor (1991) CRC Press.

Methods of the invention can also be used to ameliorate, reduce, remove, or prevent biofouling or biofilms. Biofouling is the undesirable accumulation of microorganisms, such as bacteria on structures exposed to solvent. Biofouling can occur, for example on the hulls of ships, in membrane systems, such as membrane bioreactors and reverse osmosis spiral wound membranes, water cooling systems of large industrial equipment and power stations, and oil pipelines carrying, e.g., used oils, cutting oils, soluble oils or hydraulic oils.

A biofilm can cause biofouling and is an aggregate of organisms wherein the organisms are adhered to each other, to a surface, or a combination thereof. A biofilm can comprise one or more species of bacteria, fungi, filamentous fungi, yeasts, algae, cyanobacteria, viruses, and protozoa and combinations thereof. Microorganisms present in a biofilm can be embedded within a self-produced matrix of extracellular polymeric substances. When a microorganism switches to a biofilm mode of growth, it can undergo a phenotypic shift in behavior wherein large suites of genes are differentially regulated. Nearly every species of microorganism can form biofilms. Biofilms can be found on or in living organisms or in or on non-living structures. Biofilms can be present on structures contained in naturally occurring bodies of water or man-made bodies of water, on the surface of water, surfaces exposed to moisture, interiors of pipes, cooling water systems, marine systems, boat hulls, on teeth, on plant surfaces, inside plants, on human and animal body surfaces, inside humans and animals, on contact lenses, on catheters, prosthetic cardiac valves, other prosthesis, intrauterine devices, and other structures/devices.

Biofilms can cause corrosion of metal surfaces, inhibit vessel speed, cause plant diseases, and can cause human and animal diseases. Biofilms are involved in human and animal infections, including, for example, urinary tract infections, catheter infections, middle-ear infections, dental plaque, gingivitis, dental caries, periodontal diseases, endocarditis, infections in cystic fibrosis, chronic sinusitis, and infections of permanent indwelling devices such as joint prostheses and heart valves. Biofilms can also impair cutaneous wound healing and reduce topical antibacterial efficiency in healing or treating infected skin wounds.

Some microorganisms that can form biofilms, cause biofouling and/or cause disease in humans and animals include, for example, bacteria, fungi, yeast, algae, protozoa, and viruses as described above. Biofilms can be treated in living organisms as described above. Biofilms and biofouling conditions on non-living surfaces can be treated by applying the lantibiotics of the invention onto the non-living surface or to the area surrounding the surface. Lantibiotic of the invention can also be added to the water, oil, or other fluid surrounding and in contact with the non-living surface.

The invention provides methods of ameliorating or preventing a biofouling condition or a biofilm condition, caused by one or more microorganisms, such as bacteria. The methods comprise administering one or more of the variant lantibiotics to the biofouling condition or biofilm condition, wherein the biofouling condition or biofilm condition is ameliorated.

The one or more lantibiotics can be administered to a surface that has a biofilm or biofouling condition or can be administered to a surface as a prophylactic measure. The lantibiotics can be in a dried form (e.g., lyophilized or tablet form) or a liquid solution or suspension form. The dried or liquid forms can be swabbed, poured, sprayed, flushed through the surface (e.g., pipes or membranes) or otherwise applied to the surface. Lantibiotics of the invention can be present in a composition with a carrier or diluent in an amount from about 0.001, 0.01, 0.1, 1, 5, 10, 20, 30, 40, 50, 75, 100, 150 mg/m$^2$ (or any range between about 0.001 and about 150 mg/m$^2$) and sometimes higher.

Where the biofilm is present or potentially present on an artificial surface within a human or animal (e.g., a catheter or medical device), the artificial surface can be contacted with the one or more lantibiotics prior to insertion into the human or animal. Optionally, the lantibiotics can be delivered to the surface after the artificial surface is inserted into the human or animal.

In one embodiment of the invention, a variant lantibiotic can be used for decontaminating or reducing bacterial reproduction or bacterial numbers in a biological tissue or cell culture. The lantibiotic can be present in a pharmaceutically acceptable carrier, diluent or excipient at the dosage rates as for pharmaceutical compositions described above. The lantibiotic or lantibiotic composition can be contacted with the tissue or cell culture for a period effective to substantially inhibit bacterial growth of at least one type of gram-positive bacteria. The lantibiotic can be provided in an amount effective to maintain the physiological characteristics of the biological tissue or cells and/or in an amount effective to substantially maintain the viability of the biological tissue or cells.

One embodiment of the invention provides a method for preparing isograft organs, tissues or cells, autograft tissues or cells, allograft organs, tissues or cells, xenograft organs, tissues or cells, or other cells or tissue for transplantation. The method comprises contacting the organs, cells or tissues with a lantibiotic composition of the invention for a period effective to inhibit or reduce bacterial growth or bacterial numbers of at least one type of Gram-positive bacteria. The cells, organs or tissues can be, for example, a heart valve, a blood vessel, pericardium or musculoskeletal tissue, ligaments such as anterior cruciate ligaments, knee joints, hip joints, ankle joints, meniscal tissue, skin, cornea, heart, lung, small bowel, intestine, liver, kidney, bone marrow, bone, and tendons.

The contacting step can be performed at a temperature from about 2° C. to about 42° C. for about 0.5, 1, 2, 3, 5, 10, 24, 36, or 48 hours. The lantibiotic composition can further comprise a physiological solution further comprising one or more broad spectrum antimicrobials and/or one or more antifungal agents, such as, for example vancomycin, imipenem, amikacin, and amphotericin B.

Lantibiotic compositions of the invention can also be used as a preservative for allograft and xenograft process solutions, and cell culture and tissue solutions. The solutions can comprise an effective amount of one or more lantibiotics in a physiological solution at a pH of between 3 and 8.

One or more lantibiotics of the invention can be added to foods or beverages as a preservative. Examples of foods include, processed cheese products, pasteurized dairy products, canned vegetables, high moisture, hot baked flour products, pasteurized liquid egg, natural cheese products. Lantibiotics of the invention can also be used to control *Listeria* in foods, to control spoilage by lactic acid bacteria in, e.g., beer, wine, alcohol production and low pH foods such as salad dressings. Lantibiotics of the invention can be used as an adjunct in food processing technologies such as higher pressure sterilization and electroporation. Lantibiotics can be present in a food or beverages in an amount from about 0.001, 0.01, 0.1, 1, 5, 10, 20, 30, 40, 50, 75, 100, 150, 250, 300, 400, 500, 600, 700, 800, 900, 1,000 or more mg/kg or mg/L (or any range between about 0.001 and about 1,000 mg/kg or mg/l and sometimes higher.

Figure 6:
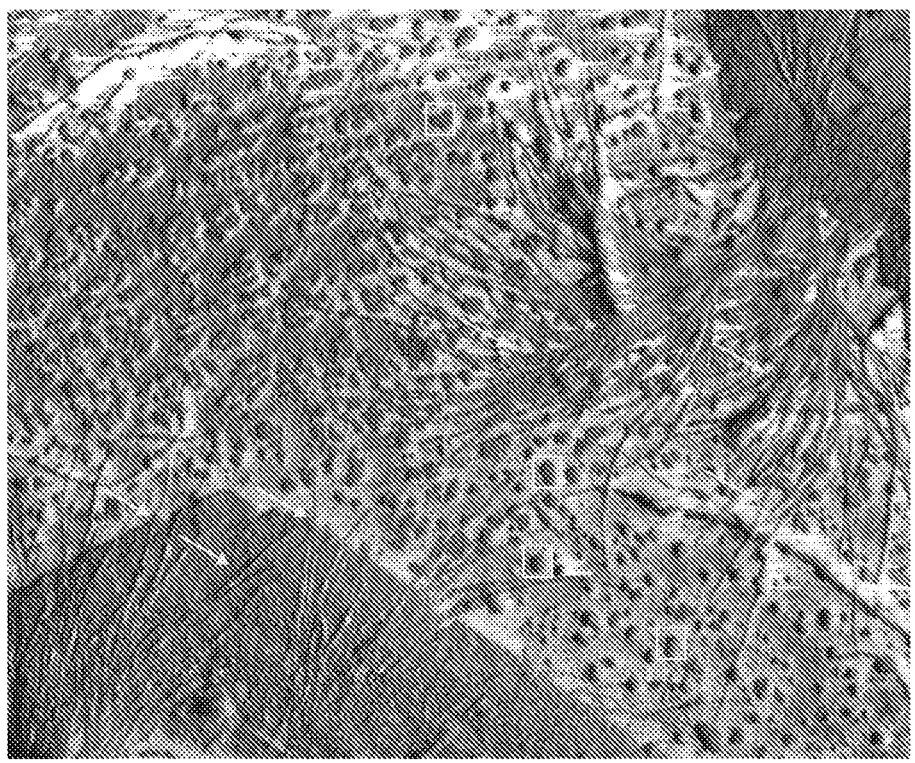
FIG. 6 shows an overlaid height and phase topography map of an atomic force microscopy image of a 5 µM gallidermin sample overlaid onto a graphite surface. Large uniform complexes (some demarcated by square boxes) and fibers (some demarcated by arrows) of gallidermin are clearly visible. Scan size=5 µm.

Lantibiotics of the invention can also be used as molecular wires, molecular switches, or molecular based memory systems. Antimicrobial peptide gallidermin solution, which is structurally similar to MU1140, was placed on a graphite surface and imaged by atomic force microscopy (AFM). FIG. 6 shows an overlay of a phase and height image. These data demonstrate the propensity for this structural class of lantibiotics to assemble into large and uniform complexes and filaments. Therefore, variant lantibiotics and wild-type lantibiotics have potential use for building nano-circuitry, as well as other nano-based applications.

Molecular wires (also known as molecular nanowires) are molecular-scale substances that conduct electrical current, which are the fundamental building blocks for molecular electronic devices. The typical diameter of molecular wires is less than three nanometers, while the length can extend to centimeters or more. A molecular wire allows the flow of electrons from one end of the wire to the other end of the wire. Molecular wires can comprise at least two terminals for contacting additional components of a nano-electronic device.

A molecular switch (also known as a controllable wire) is a molecular structure where the electron flow can be turned on and off on demand. A molecular based memory system is one or more molecule wires or switches that have the ability to alter its conductivity by storing electrons.

A molecular wire, switch, or molecular based memory system can be present on or anchored to substrates such as silicon wafers, synthetic polymer supports, glass, agarose, nitrocellulose, nylon, Au, Cu, Pd, Pt, Ni, Al, $Al_2O_3$, nickel grids or disks, carbon supports, aminosilane-treated silica, polylysine coated glass, mica, and semiconductors.

Kits

Compositions of the invention can be present in a kit comprising a container of one or more lantibiotics of the invention. The lantibiotics can be lyophilized and in the form of a lyophilized powder or tablet or can be in a solution or suspension optionally with buffers, excipients, diluents, adjuvants, or pharmaceutically acceptable carriers. A kit can also comprise one or more applicators for the one or more lantibiotics to a body part or tissue or surface. The applicator can be, for example, a swab, a syringe (with or without a needle), a dropper, a sprayer, a surgical dressing, wound packing, or a bandage. Optionally, the kit can comprise one or more buffers, diluents, adjuvants, therapeutically acceptable carriers, or pharmaceutically acceptable carriers for reconstituting, diluting, or preparing the one or more variant MU1140 lantibiotics.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Mutagenesis of MU1140

The *Streptococcus mutans* genome database and lan gene cluster, GenBank/EMBL accession number (AF051560), was used to design primers for the mutagenesis and sequencing work. The open reading frame (ORF) of the native MU1140 structural gene (lanA) plus 500 base pairs (bp) of 5' and 3' flanking DNA was cloned into the pVA891 plasmid to create p190. The cloned insert in p190 was derived by PCR amplification of chromosomal DNA of *Streptococcus mutans* strain JH1140 (ATCC 55676) using the primer sequences of SRWlanA_1 and SRWlanA_2 (see FIG. 2). Reagents and media were purchased from Fisher Scientific, enzymes were purchased from New England BioLabs, and primers were purchased from Integrated DNA Technologies (IDT) unless otherwise stated.

Polymerase Chain Reaction (PCR)

Mutations (see FIG. 1B) were introduced into the propeptide region of lanA, the structural gene for MU1140, to create the variants of MU1140. See FIG. 3. The p190 plasmid (J. D. Hillman, unpublished) was used as a template and the site specific mutations were introduced using two-step PCR. In the first step, the upstream and downstream outside primers (SRWlanA_1 and SRWlanA_2) were paired with appropriate inside primers (e.g., SRWlanA_1/Trp4Ala_2 and SRWlanA_2/Trp4Ala_1) (FIG. 2), one of which was synthesized to contain an altered base sequence relative to the wild type sequence. The result of this step was the production of two fragments, one that included 5' flanking DNA and a portion of lanA, including the site directed base alterations. The second fragment contained the remainder of lanA plus 3' flanking DNA. Primers used to produce the MU1140 variants are found in FIG. 2. The two fragments were then mixed in equal amounts and subjected to a second round of PCR using the two outside primers, SRWlanA_1 and SRWlanA_2, to yield the final amplicon.

PCR reactions were performed using Taq polymerase in a final volume of 50 µL containing 0.4 µmol of each primer, 50 ng of template DNA, 0.016 mM dNTP, and 1 unit of DNA polymerase in 1× polymerase buffer. Amplification conditions for each fragment were as follows: preheat at 95° C. for 1 min, followed by 27 cycles incubation with denaturation (95° C.) for 30 sec, annealing (56° C.) for 30 sec and extension (72° C.) for 2 min followed by a final extension (72° C.) for 10 min. Both fragments were combined 50:50 and amplified using the two outside primers SRWlanA_1 and SRWlanA_2 under the same amplification conditions as mentioned above.

The final PCR product was ligated into a TOPO-TA vector (Invitrogen, Carlsbad, Calif.) following kit directions and transformed into DH5α-T1® cells (Invitrogen) using standard methods and spread on LB plates containing 50 µg/mL of ampicillin and 40 µL of X-gal (40 mg/mL). Blue-white screening was utilized to identify colonies containing an insert. Plasmid DNA from each colony was purified using a PureYield Plasmid Miniprep System (Promega, Madison, Wis.) according to the manufacturer's instructions. Purified plasmid was subjected to restriction digest using EcoRI and examined by agarose gel electrophoresis to identify those that have a cloned insert of proper size (~1100 bp). Plasmids containing the proper sized insert were sequenced using M13 Forward (−20) primer, 5'-GTAAAACGACGGCCAG-3' (SEQ ID NO:18), to confirm the proper insertion, deletion, or replacement of nucleotide bases.

Recombination

Restriction enzyme digestion was performed on purified plasmid from colonies harboring a confirmed mutation. The insert were separated from the TOPO plasmid by electrophoresis, excised from the gel, and purified using a Qiagen Gel Extraction Kit (Qiagen, Valencia, Calif.). The purified insert was then ligated into the *S. mutans* suicide vector, pVA891, in a 3:1 insert:vector ratio using T4 DNA ligase at 16° C. overnight. The resultant plasmid was then transformed into DH5α cells using standard methods and spread on LB plates containing 300 µg/mL of erythromycin. Colonies which arose following incubation were analyzed to verify proper insert size and sequence as described above.

Purified pVA891 DNA containing confirmed inserts was transformed into *S. mutans* strain JH1140 (ATCC 55676) as follows: *S. mutans* was grown overnight then diluted 1:15 in fresh THyex broth (30 g/L THB, 3 g/L yeast extract), 200 µL of diluted cells were added to a 96 well plate and incubated at 37° C. for 2 hours. Two microliters of competence stimulating peptide (CSP, 0.1 µg/mL) was added, and plates were incubated for an additional 6 hours. See Li et al., (2002) J. Bacteriol. 184:2699. Fifty microliters of cells were then plated onto pre-warmed THyex agar plates (30 g/L THB, 3 g/L yeast extract, and 15 g/L of nutrient agar) containing 300 µg/mL of erythromycin and incubated at 37° C. for 48 hours. Genomic DNA was extracted from clones that arose utilizing a standard chloroform/phenol extraction method and the DNA was used as template for PCR that used SRWlanA_1 and SRWlanA_2 to identify heterodiploid clones presumed to have one wild type and one mutated copy of the lanA gene separated by vector DNA, as previously described by Hillman et al., (2000) Infect. Immun. 68:543-549.

Confirming Genetic Identity of Mutant Constructs

Clones containing the desired lanA mutations were obtained by spontaneous resolution of the heterodiploid state as follows: several confirmed heterodiploids were grown overnight in 20 mL THyex broth that did not contain erythromycin. The cultures were subcultured (1:20 dilution into fresh media) and again grown overnight to saturation. The cultures were then diluted 100,000 fold and spread onto large THyex agar plates and incubated at 37° C. for 48 hours. Resultant colonies were replica patched onto medium with and without erythromycin to identify spontaneous recombinants in which elimination of the pVA891 plasmid (expressing the erythromycin resistance gene) and either the wild-type or mutated lanA gene had occurred. Erythromycin sensitive colonies that were identified from the replica plating technique were re-tested on medium with and without erythromycin. The lanA region of erythromycin sensitive clones was amplified by PCR as described above. The amplicons generated were sequenced to identify clones possessing only the modified lanA genes. BLAST sequence analysis was used to compare the wild-type sequence of lanA to the suspected mutants' (FIG. 3). The mutants generated were: Phe1Ile, Phe1Gly, Trp4Ala, Trp4insAla, ΔTrp4, Dha5Ala, Ala$_s$7insAla, and Arg13Asp.

Example 2

Bioactivity of Mutants

The parent *S. mutans* strain, JH1140 (ATCC 55676), and the mutants were grown to an $OD_{600}$ of 0.8 and diluted to an $OD_{600}$ of 0.2. Samples (2 µL) of the cultures were spotted in triplicate on a pre-warmed THyex agar plate (150×15 mm) and allowed to air dry. This assay was performed in this manner to help ensure that each sample had the same colony size for comparing zones of inhibition. The plate was incubated for 24 hours at 37° C., and then placed in an oven at 55° C. for thirty minutes to kill the bacteria before the *M. luteus* ATCC 272 indicator strain was overlaid in molten top agar. Heat killing the bacteria prevented any further antimicrobial compound production. *M. luteus* ATCC 272 was grown to an OD $600_{nm}$ between 0.4 and 0.8 and diluted to an OD$600_{nm}$ of 0.2. Then, 400 µl of these cells was added to 10 ml of molten top agar (42° C.) (30 g/L Todd Hewitt Broth and 7.5 g/L Nutrient agar). All 10 milliliters of top agar containing the standardized suspension was added to each plate containing approximately 50 ml of THyex agar. The plates were allowed to solidify before being inverted and incubated overnight at 37° C. Each inhibitory zone radius was measured in mm from one edge of the colony to the farthest portion of the zone. The area of the inhibitory zone was calculated for each zone and compared to the average zone area of the wild-type (n=10).

Figure 8:
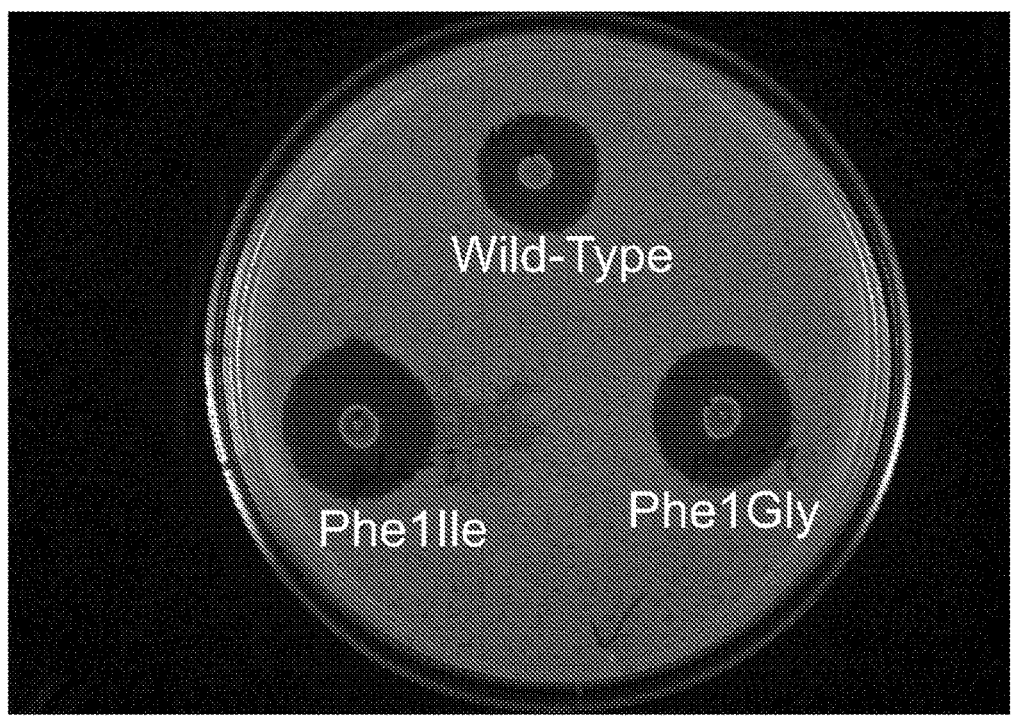
FIG. 8 shows the results of the zone of inhibition plate assays for Phe1Ile and Phe1Gly variants.

FIG. 4 illustrates the bioactivity of strains producing variants of MU1140 compared to wild-type MU1140. The results are summarized in FIG. 5, which shows that the strains producing Trp4insAla and ΔTrp4 had zones that were not significantly different (Student's t test, p>0.05) than the wild-type. The strain producing Arg13Asp had the largest inhibitory zone area amounting to a 2.57-fold increase relative to wild-type (p<0.001). The strains producing Trp4Ala and Dha5Ala produced significant (p<0.001) 2.12-fold and 1.87-fold increases, respectively, relative to the wild-type. The strain producing Ala$_s$7insAla had the smallest zone area, which amounted to a significant (p<0.001) ca. 2-fold reduction in zone area when compared to the wild-type. FIG. 8 shows the biological activity of strains producing other variants of MU1140 (Phe1Ile and Phe1Gly) compared to wild-type MU1140. The strains producing Phe1Ile and Phe1Gly demonstrated significant (p<0.001) 1.82-fold and 1.57-fold increases, respectively, relative to the wild-type.

Preliminary studies involving purification of the variant molecules indicated that they were all made by their respective mutant strains in amounts equal to the wild-type strain. This result indicates that the changes in the areas of the zones of inhibition were the result of changes in the bioactivity of the variant molecules rather than changes in the levels of their production and/or excretion into the environment.

Example 3

Minimum Inhibitory Concentration

Wild-type mutacin 1140, mutacin 1140 with a F1I mutation, mutacin 1140 with a W4A mutation, and mutacin 1140 with a R13D mutation was purified to about 90% purity (measured via HPLC). The minimum inhibitory concentration (MIC) of MU1140 and variants of MU1140 was determined against several bacteria. The MIC is the lowest concentration of MU1140 that will inhibit the visible growth of a microorganism after 24 hour incubation. A lower MIC is an indication of greater inhibitory activity. Preparation of the antimicrobial agent and bacterial inoculum for minimum inhibitory concentrations (MICs) was performed by following the method described in Clinical Laboratory Standard Institute (CLSI) M07-8A with some minor modifications. *Streptococcus mutans* UA159 was tested overnight in a shaking incubator to maintain uniform dispersion of the bacteria. *Clostridium difficile* UK1 was tested in an anaerobic chamber at 37° C. The medium used was THyex. The results are shown in Table 1.

TABLE 1

| MU1140 Variant | *Streptococcus mutans* UA159 | *Streptococcus pneumonia* FA1 | *Staphylococcus aureus* FA1 | *Micrococcus luteus* ATCC10240 | *Clostridium difficile* UK1 |
|---|---|---|---|---|---|
| Mu1140 Wild-type | 2 | 0.5 | 16 | 0.0625 | 16 |
| Mu1140 F1I | 2 | 0.25 | 8 | 0.0156 | 8 |
| Mu1140W4A | 2 | 0.125 | 16 | 0.0312 | 8 |
| Mu1140R13D | 2 | 4 | >16 | 0.125 | 16 |

While the MIC is not necessarily lower for each organism for each mutant, each mutant may still have advantages over the wild-type MU1140 because it may, for example, be easier to produce, easier to transport, have better shelf stability, have better serum stability, or have better proteolytic stability, among other advantageous properties.

Discussion

There has been a number of studies that used site directed mutagenesis of the structural gene for nisin and certain other lantibiotics (reviewed by Chatterjee et al. (2005) Chem. Rev. 105:633) to analyze the importance of particular amino acids in the activity of these molecules. Rarely have these mutations resulted in increased bioactivity. Mutations that increase activity are important from the standpoint of using lantibiotics as therapeutic agents or in other applications, since a reduction in the amount of lantibiotic needed for administration would obviously improve the cost of goods. An additional benefit in the case of use as a drug is the potential to improve the therapeutic index.

As an independent consideration, certain amino acid substitutions and deletions that increase or do not change the bioactivity of the native molecule may facilitate manufacturing of a lantibiotic. This is particularly true in the instance where the lantibiotic is chemically synthesized, e.g., using DPOLT (U.S. Pat. No. 7,521,529; U.S. Publ. No. 2009/0215985).

The Phe1Ile and Phe1Gly mutants yielded products with significant increases in activity, as measured by the zone of inhibition assay. One or both of these mutations may improve MU1140 by reducing the amount needed for application, thereby decreasing the cost of goods and improving its therapeutic index.

The Trp4insAla mutant yielded a product that had bactericidal activity similar to wild-type MU1140. The same result was seen for the deletion of tryptophan at position 4. The mutation replacing tryptophan at position 4 with alanine resulted in a significant increase in bioactivity when compared to the wild-type. One of these mutations may benefit manufacture using DPOLT-based synthesis, particularly in the event that closure of ring A is facilitated.

Replacement of Dha, a residue that starts out as a serine and is later dehydrated during post-translation modification, with alanine also results in a significant increase in bioactivity. When this same mutation was made in nisin, the product showed similar bioactivity when compared to wild-type nisin. Chan et al. (1996) Applied and Environmental Microbiology 62:2966-2969. This mutation is very useful as it reduces the number of dehydrated residues in MU1140, thereby potentially facilitating manufacture and decreasing the cost of goods.

Addition of an alanine after $_S$Ala at position 7 resulted in a significant reduction in bioactivity. The addition of a residue would also increase the complexity of making synthetic MU1140, and so this variant is not considered to be of any value.

The most interesting result was obtained for the Arg13Asp mutant. This mutation resulted in an unexpected, highly significant increase in bioactivity when compared to the wild-type. Here there was replacement of a positively charged residue with a negatively charged residue in the hinge region. This finding is contrary to the conventional belief that negative charges for lantibiotics should reduce bioactivity since positive charges are thought to aid in the interaction of the antibiotic with negatively charged lipids present in the target cell membrane. This mutation also removed a trypsin cleavable site from the compound, thereby making it more stable to enzymatic hydrolysis.

We claim:

1. A variant MU1140 lantibiotic comprising Formula I:

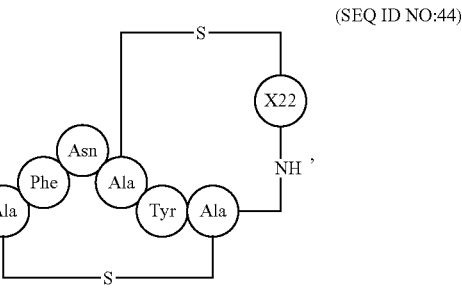

(SEQ ID NO:44)

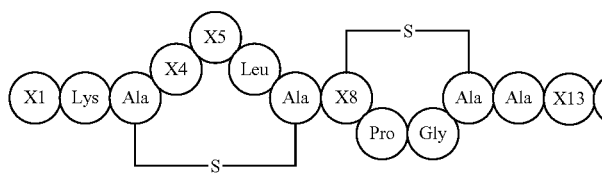

wherein the X at position 1 is Gly, the X at position 4 is Trp, the X at position 5 is Dha, the X at position 13 is Arg, the X at position 8 is Abu or Ala, the X at position 14 is Dhb or Ala, and the X at position 22 is —CH=CH— or —CH$_2$—CH$_2$—;

(i) wherein the X at position 1 is Phe, the X at position 4 is Ala, absent, or both Trp and Ala, the X at position 5 is Dha, the X at position 13 is Arg, the X at position 8 is Abu or Ala, the X at position 14 is Dhb or Ala, and the X at position 22 is —CH=CH— or —CH$_2$—CH$_2$—;

(ii) wherein the X at position 1 is Phe, the X at position 4 is Trp, the X at position 5 is Ala, the X at position 13 is Arg, the X at position 8 is Abu or Ala, the X at position 14 is Dhb or Ala, and the X at position 22 is —CH=CH— or —CH$_2$—CH$_2$—;

(iii) wherein the X at position 1 is Phe, the X at position 4 is Trp, the X at position 5 is Dha, the X at position 13 is Asp, the X at position 8 is Abu or Ala, the X at position 14 is Dhb or Ala, and the X at position 22 is —CH=CH— or —CH$_2$—CH$_2$—;

(iv) wherein the X at position 1 is Gly or Ile, the X at position 4 is Ala, absent, or both Trp and Ala, the X at position 5 is Dha, the X at position 13 is Arg, the X at position 8 is Abu or Ala, the X at position 14 is Dhb or Ala, and the X at position 22 is —CH=CH— or —CH$_2$—CH$_2$—;

(v) wherein the X at position 1 is Gly or Ile, the X at position 4 is Trp, the X at position 5 is Ala, the X at position 13 is Arg, the X at position 8 is Abu or Ala, the X at position 14 is Dhb or Ala, and the X at position 22 is —CH=CH— or —CH$_2$—CH$_2$—;

(vi) wherein the X at position 1 is Gly or Ile, the X at position 4 is Trp, the X at position 5 is Dha, the X at position 13 is Asp, the X at position 8 is Abu or Ala, the X at position 14 is Dhb or Ala, and the X at position 22 is —CH=CH— or —CH$_2$—CH$_2$—;

(vii) wherein the X at position 1 is Phe, the X at position 4 is Ala, absent, or both Trp and Ala, the X at position 5 is Ala, the X at position 13 is Arg, the X at position 8 is Abu or Ala, the X at position 14 is Dhb or Ala, and the X at position 22 is —CH=CH— or —CH$_2$—CH$_2$—;

(viii) wherein the X at position 1 is Phe, the X at position 4 is Ala, absent, or both Trp and Ala, the X at position 5 is Dha, the X at position 13 is Asp, the X at position 8 is Abu or Ala, the X at position 14 is Dhb or Ala, and the X at position 22 is —CH=CH— or —CH$_2$—CH$_2$—;

(ix) wherein the X at position 1 is Phe, the X at position 4 is Trp, the X at position 5 is Ala, the X at position 13 is Asp, the X at position 8 is Abu or Ala, the X at position 14 is Dhb or Ala, and the X at position 22 is —CH=CH— or —CH$_2$—CH$_2$—;

(x) wherein the X at position 1 is Gly or Ile, the X at position 4 is Ala, absent, or both Trp and Ala, the X at position 5 is Ala, the X at position 13 is Arg, the X at position 8 is Abu or Ala, the X at position 14 is Dhb or Ala, and the X at position 22 is —CH=CH— or —CH$_2$—CH$_2$—;

(xi) wherein the X at position 1 is Gly or Ile, the X at position 4 is Ala, absent, or both Trp and Ala, the X at position 5 is Dha, the X at position 13 is Asp, the X at position 8 is Abu or Ala, the X at position 14 is Dhb or Ala, and the X at position 22 is —CH=CH— or —CH$_2$—CH$_2$—;

(xii) wherein the X at position 1 is Gly or Ile, the X at position 4 is Trp, the X at position 5 is Ala, the X at position 13 is Asp, the X at position 8 is Abu or Ala, the X at position 14 is Dhb or Ala, and the X at position 22 is —CH=CH— or —CH$_2$—CH$_2$—;

(xiii) wherein the X at position 1 is Phe, the X at position 4 is Ala, absent, or both Trp and Ala, the X at position 5 is Ala, the X at position 13 is Asp, the X at position 8 is Abu or Ala, the X at position 14 is Dhb or Ala, and the X at position 22 is —CH=CH— or —CH$_2$—CH$_2$—;

(xiv) wherein the X at position 1 is Gly or Ile, the X at position 4 is Ala, absent, or both Trp and Ala, the X at position 5 is Ala, the X at position 13 is Asp, the X at position 8 is Abu or Ala, the X at position 14 is Dhb or Ala, and the X at position 22 is —CH=CH— or —CH$_2$—CH$_2$—;

or a pharmaceutically acceptable salt thereof.

2. An antimicrobial composition comprising one or more isolated variant MU1140 lantibiotics of claim 1 and a pharmaceutically acceptable carrier, pharmaceutically acceptable diluent, other diluent or excipient.

3. The antimicrobial composition of claim 2, wherein the composition further comprises at least one antifungal agent, one additional antimicrobial agent, a membrane disrupting agent, or combinations thereof.

4. The antimicrobial composition of claim 3, wherein the one additional antimicrobial agent has Gram negative bacteriostatic or bactericidal activity and the membrane disrupting agent renders Gram negative bacteria susceptible to the variant MU1140 lantibiotic.

5. The antimicrobial composition of claim 2, wherein the one or more isolated MU1140 lantibiotics are present in the composition at about 0.001, 0.01, 0.1, 1, 5, 10, 20, 30, 40, 50, 75, 100, 150, 200, 300, 400, 500, 600, 700, 800, 900, 1,000 or more mg/kg or mg/L.

6. A method of reducing reproduction of bacteria or reducing numbers of bacteria present in or on in a subject, comprising administering to the subject a therapeutically effective amount of the antimicrobial composition of claim 2.

7. The method of claim 6, wherein the subject is a human.

8. The method of claim 6, wherein the composition is administered orally or topically, nasally, buccally, sublingually, transmucosally, rectally, transdermally, by inhalation, by injection or intrathecally.

9. The method of claim 8, wherein the injection is intramuscular, intravenous, intrapulmonary, intramuscular, intradermal, intraperitoneal, intrathecal, or subcutaneous injection.

10. A preservative comprising an effective amount of one or more variant MU1140 lantibiotics of claim 1 in a physiological solution at a pH of between 3 and 8.

11. A food, beverage, gum, or dentifrice composition comprising an amount of one or more variant MU1140 lantibiotics of claim 1 sufficient to reduce the reproduction of bacteria or numbers of bacteria in the composition.

12. A method of reducing reproduction of bacteria or reducing numbers of bacteria present in or on a composition or object, comprising contacting the antimicrobial composition of claim 10 with the composition or object for a period effective to reduce reproduction of bacteria or reduce numbers of bacteria in or on the composition or object.

13. The method of claim 12, wherein the composition is a food, beverage, gum, or dentifrice.

14. A purified polynucleotide comprising SEQ ID NOs: 19-26 or combinations thereof.

15. A composition comprising a solid surface or a woven or non-woven textile with the variant MU1140 lantibiotic of claim 1 or coated onto, immobilized, linked, or bound to the solid surface or textile.

16. A method of reducing a biofilm or biofouling condition comprising contacting the variant MU1140 lantibiotic of claim 1 with the biofilm or biofouling condition for a period effective to reduce reproduction of bacteria or reduce numbers of bacteria in or on the biofilm or biofouling condition.

17. A kit comprising one or more variant MU1140 lantibiotics of claim 1 and one or more applicators.

18. A variant MU1140 lantibiotic comprising Formula I:

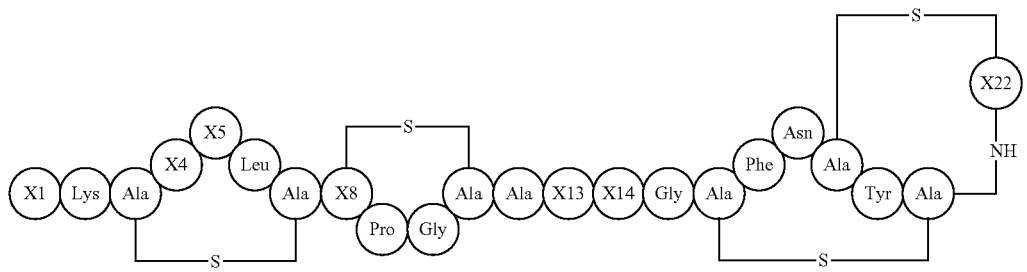

wherein the X at position 1 is Ile, the X at position 4 is Trp, the X at position 5 is Dha, the X at position 13 is Arg, the X at position 8 is Abu or Ala, the X at position 14 is Dhb or Ala, and the X at position 22 is —CH=CH— or —CH$_2$—CH$_2$—, or a pharmaceutically acceptable salt thereof.

19. An antimicrobial composition comprising one or more isolated variant MU1140 lantibiotics of claim 18 and a pharmaceutically acceptable carrier, pharmaceutically acceptable diluent, other diluent or excipient, or physiological solution at a pH of between 3 and 8.

20. A method of reducing reproduction of bacteria or reducing numbers of bacteria present in or on in a subject, object, or composition, comprising administering to the subject, object, or composition an effective amount of the antimicrobial composition of claim 18.

\* \* \* \* \*

SEQUENCE LISTING

<160> NUMBER OF SEQ ID NOS: 44

<210> SEQ ID NO 1
<211> LENGTH: 33
<212> TYPE: DNA
<213> ORGANISM: Artificial Sequence
<220> FEATURE:

<223> OTHER INFORMATION: Synthetic

<400> SEQUENCE: 1
agaattcagg atgctatcgc tgcttttttt gtg      33

<210> SEQ ID NO 2
<211> LENGTH: 32
<212> TYPE: DNA
<213> ORGANISM: Artificial Sequence
<220> FEATURE:
<223> OTHER INFORMATION: Synthetic

<400> SEQUENCE: 2
agaattcagg aaagttgcca tatggttttg tg      32

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
gcaagccttt gtacgcctgg ttg      23

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
acaaaggctt gcacttttga aacg      24

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gcaagccttt gtacgcctgg ttg      23

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
caaaggcttg cccaactttt gaaacg      26

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
agcctttgta cgcctggttg      20

```
<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
cgtacaaagg ctactttga aacg                                                 24

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
gcactttgta cgcctggttg tgc                                                 23

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
ggcgtacaaa gtgcccaact tttgaa                                              26

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
gcaacgcctg gttgtgcaag gac                                                 23

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
accaggcgtt gcacaaaggc tcc                                                 23

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
gacacaggta gtttcaatag ttac                                                24

<210> SEQ ID NO 14
<211> LENGTH: 26
<212> TYPE: DNA
<213> ORGANISM: Artificial Sequence
<220> FEATURE:
<223> OTHER INFORMATION: Synthetic
```

-continued

```
<400> SEQUENCE: 14
gaaactacct gtgtctgcac aaccag                                          26

<210> SEQ ID NO 15
<211> LENGTH: 66
<212> TYPE: DNA
<213> ORGANISM: Artificial Sequence
<220> FEATURE:
<223> OTHER INFORMATION: Synthetic

<400> SEQUENCE: 15
ttcaaaagtt ggagcctttg tacgcctggt tgtgcaagga caggtagttt caatagttac      60
tgttgc                                                                66

<210> SEQ ID NO 16
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Ile or Gly
<220> FEATURE:
<221> NAME/KEY: DISULFID
<222> LOCATION: (3)..(8)
<220> FEATURE:
<221> NAME/KEY: MISC_FEATURE
<222> LOCATION: (4)..(4)
<223> OTHER INFORMATION: X is Trp, Ala, or absent
<220> FEATURE:
<221> NAME/KEY: MISC_FEATURE
<222> LOCATION: (10)..(10)
<223> OTHER INFORMATION: X is Abu amino acid or Ala
<220> FEATURE:
<221> NAME/KEY: DISULFID
<222> LOCATION: (10)..(13)
<220> FEATURE:
<221> NAME/KEY: MISC_FEATURE
<222> LOCATION: (16)..(16)
<223> OTHER INFORMATION: X is Dhb amino acid or Ala
<220> FEATURE:
<221> NAME/KEY: DISULFID
<222> LOCATION: (18)..(23)
<220> FEATURE:
<221> NAME/KEY: MISC_FEATURE
<222> LOCATION: (21)..(23)
<223> OTHER INFORMATION: lanthionine bridge

<400> SEQUENCE: 16

Xaa Lys Ala Xaa Ala Ala Leu Ala Ala Xaa Pro Gly Ala Ala Asp Xaa
1               5                   10                  15

Gly Ala Phe Asn Ala Tyr Ala
            20

<210> SEQ ID NO 17
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: DISULFID
```

```
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: MISC_FEATURE
<222> LOCATION: (14)..(14)
<223> OTHER INFORMATION: X is Dhb amino acid
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: lanthionine bridge

<400> SEQUENCE: 17

Phe Lys Ala Trp Xaa Leu Ala Xaa Pro Gly Ala Ala Arg Xaa Gly Ala
1               5                   10                  15

Phe Asn Ala Tyr Ala
            20

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
gtaaaacgac ggccag                                                   16

<210> SEQ ID NO 19
<211> LENGTH: 66
<212> TYPE: DNA
<213> ORGANISM: Artificial Sequence
<220> FEATURE:
<223> OTHER INFORMATION: Synthetic

<400> SEQUENCE: 19
ttcaaaagtg caagcctttg tacgcctggt tgtgcaagga caggtagttt caatagttac   60
tgttgc                                                              66

<210> SEQ ID NO 20
<211> LENGTH: 69
<212> TYPE: DNA
<213> ORGANISM: Artificial Sequence
<220> FEATURE:
<223> OTHER INFORMATION: Synthetic

<400> SEQUENCE: 20
ttcaaaagtt gggcaagcct ttgtacgcct ggttgtgcaa ggacaggtag tttcaatagt   60
tactgttgc                                                           69

<210> SEQ ID NO 21
<211> LENGTH: 63
<212> TYPE: DNA
<213> ORGANISM: Artificial Sequence
<220> FEATURE:
<223> OTHER INFORMATION: Synthetic

<400> SEQUENCE: 21
ttcaaaagta gcctttgtac gcctggttgt gcaaggacag gtagtttcaa tagttactgt   60
tgc                                                                 63
```

<210> SEQ ID NO 22
<211> LENGTH: 66
<212> TYPE: DNA
<213> ORGANISM: Artificial Sequence
<220> FEATURE:
<223> OTHER INFORMATION: Synthetic

<400> SEQUENCE: 22
ttcaaaagtt gggcactttg tacgcctggt tgtgcaagga caggtagttt caatagttac    60
tgttgc    66

<210> SEQ ID NO 23
<211> LENGTH: 69
<212> TYPE: DNA
<213> ORGANISM: Artificial Sequence
<220> FEATURE:
<223> OTHER INFORMATION: Synthetic

<400> SEQUENCE: 23
ttcaaaagtt ggagcctttg tgcaacgcct ggttgtgcaa ggacaggtag tttcaatagt    60
tactgttgc    69

<210> SEQ ID NO 24
<211> LENGTH: 66
<212> TYPE: DNA
<213> ORGANISM: Artificial Sequence
<220> FEATURE:
<223> OTHER INFORMATION: Synthetic

<400> SEQUENCE: 24
ttcaaaagtt ggagcctttg tacgcctggt tgtgcagaca caggtagttt caatagttac    60
tgttgc    66

<210> SEQ ID NO 25
<211> LENGTH: 66
<212> TYPE: DNA
<213> ORGANISM: Artificial Sequence
<220> FEATURE:
<223> OTHER INFORMATION: Synthetic

<400> SEQUENCE: 25
ggcaaaagtt ggagcctttg tacgcctggt tgtgcaagga caggtagttt caatagttac    60
tgttgc    66

<210> SEQ ID NO 26
<211> LENGTH: 66
<212> TYPE: DNA
<213> ORGANISM: Artificial Sequence
<220> FEATURE:
<223> OTHER INFORMATION: Synthetic

<400> SEQUENCE: 26
atcaaaagtt ggagcctttg tacgcctggt tgtgcaagga caggtagttt caatagttac    60
tgttgc    66

<210> SEQ ID NO 27
<211> LENGTH: 39
<212> TYPE: DNA
<213> ORGANISM: Artificial Sequence
<220> FEATURE:
<223> OTHER INFORMATION: Synthetic

<400> SEQUENCE: 27
gatccagata ctcgtggcaa aagttggagc ctttgtacg    39

<210> SEQ ID NO 28
<211> LENGTH: 34
<212> TYPE: DNA
<213> ORGANISM: Artificial Sequence
<220> FEATURE:
<223> OTHER INFORMATION: Synthetic

<400> SEQUENCE: 28
caacttttgc cacgagtatc tggatcgtcg ttgc    34

<210> SEQ ID NO 29
<211> LENGTH: 39
<212> TYPE: DNA
<213> ORGANISM: Artificial Sequence
<220> FEATURE:
<223> OTHER INFORMATION: Synthetic

<400> SEQUENCE: 29
gatccagata ctcgtatcaa aagttggagc ctttgtacg    39

<210> SEQ ID NO 30
<211> LENGTH: 34
<212> TYPE: DNA
<213> ORGANISM: Artificial Sequence
<220> FEATURE:
<223> OTHER INFORMATION: Synthetic

<400> SEQUENCE: 30 caactttga tacgagtatc tggatcgtcg ttgc    34

<210> SEQ ID NO 31
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: DISULFID
<222> LOCATION: (13)..(19)
<220> FEATURE:
<221> NAME/KEY: MISC_FEATURE
<222> LOCATION: (15)..(15)
<223> OTHER INFORMATION: or Ala
<220> FEATURE:
<221> NAME/KEY: MISC_FEATURE
<222> LOCATION: (21)..(21)
<223> OTHER INFORMATION: or Met
<220> FEATURE:
<221> NAME/KEY: MOD_RES
<222> LOCATION: (23)..(23)
<223> OTHER INFORMATION: Abu

```
<220> FEATURE:
<221> NAME/KEY: DISULFID
<222> LOCATION: (23)..(25)
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (26)..(28)
<220> FEATURE:
<221> NAME/KEY: MISC_FEATURE
<222> LOCATION: (27)..(27)
<223> OTHER INFORMATION: or His
<220> FEATURE:
<221> NAME/KEY: MISC_FEATURE
<222> LOCATION: (33)..(33)
<223> OTHER INFORMATION: X is Dha

<400> SEQUENCE: 31

Ile Xaa Ala Ile Xaa Leu Ala Xaa Pro Gly Ala Lys Xaa Gly Val Leu
1               5                   10                  15

Met Gly Ala Asn Leu Lys Xaa Ala Xaa Ala Asn Ala Ser Val His Val
            20                  25                  30

Xaa Lys

<210> SEQ ID NO 32
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: MOD_RES
<222> LOCATION: (13)..(13)
<223> OTHER INFORMATION: Abu
<220> FEATURE:
<221> NAME/KEY: DISULFID
<222> LOCATION: (13)..(19)
<220> FEATURE:
<221> NAME/KEY: MOD_RES
<222> LOCATION: (23)..(23)
<223> OTHER INFORMATION: Abu
<220> FEATURE:
<221> NAME/KEY: DISULFID
<222> LOCATION: (23)..(25)
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (26)..(28)
<220> FEATURE:
<221> NAME/KEY: MISC_FEATURE
<222> LOCATION: (27)..(27)
<223> OTHER INFORMATION: or His
```

```
<220> FEATURE:
<221> NAME/KEY: MISC_FEATURE
<222> LOCATION: (33)..(33)
<223> OTHER INFORMATION: X is Dha amino acid

<400> SEQUENCE: 32

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile His Val
            20                  25                  30

Xaa Lys

<210> SEQ ID NO 33
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: DISULFID
<222> LOCATION: (13)..(19)
<220> FEATURE:
<221> NAME/KEY: MOD_RES
<222> LOCATION: (13)..(13)
<223> OTHER INFORMATION: Abu
<220> FEATURE:
<221> NAME/KEY: DISULFID
<222> LOCATION: (23)..(25)
<220> FEATURE:
<221> NAME/KEY: MOD_RES
<222> LOCATION: (23)..(23)
<223> OTHER INFORMATION: Abu
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (26)..(28)
<220> FEATURE:
<221> NAME/KEY: MISC_FEATURE
<222> LOCATION: (27)..(27)
<223> OTHER INFORMATION: or His
<220> FEATURE:
<221> NAME/KEY: MISC_FEATURE
<222> LOCATION: (30)..(30)
<223> OTHER INFORMATION: or Ile
<220> FEATURE:
<221> NAME/KEY: MISC_FEATURE
<222> LOCATION: (33)..(33)
<223> OTHER INFORMATION: X is Dha amino acid

<400> SEQUENCE: 33

Ile Xaa Ala Ile Xaa Leu Ala Xaa Pro Gly Ala Lys Xaa Gly Ala Leu
1               5                   10                  15
```

Met Gly Ala Asn Met Lys Xaa Ala Xaa Ala Asn Ala Ser Val His Val
            20                  25                  30

Xaa Lys

<210> SEQ ID NO 34
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: MOD_RES
<222> LOCATION: (13)..(13)
<223> OTHER INFORMATION: Abu
<220> FEATURE:
<221> NAME/KEY: DISULFID
<222> LOCATION: (13)..(19)
<220> FEATURE:
<221> NAME/KEY: MISC_FEATURE
<222> LOCATION: (15)..(15)
<223> OTHER INFORMATION: or Ala
<220> FEATURE:
<221> NAME/KEY: MISC_FEATURE
<222> LOCATION: (18)..(18)
<223> OTHER INFORMATION: or Gly
<220> FEATURE:
<221> NAME/KEY: MISC_FEATURE
<222> LOCATION: (18)..(18)
<223> OTHER INFORMATION: X is Dhb amino acid
<220> FEATURE:
<221> NAME/KEY: MISC_FEATURE
<222> LOCATION: (20)..(20)
<223> OTHER INFORMATION: or Asn
<220> FEATURE:
<221> NAME/KEY: MISC_FEATURE
<222> LOCATION: (21)..(21)
<223> OTHER INFORMATION: or Met
<220> FEATURE:
<221> NAME/KEY: MOD_RES
<222> LOCATION: (23)..(23)
<223> OTHER INFORMATION: Abu
<220> FEATURE:
<221> NAME/KEY: DISULFID
<222> LOCATION: (23)..(25)
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (26)..(28)
<220> FEATURE:
<221> NAME/KEY: MISC_FEATURE
<222> LOCATION: (27)..(27)
<223> OTHER INFORMATION: or His
<220> FEATURE:
<221> NAME/KEY: MISC_FEATURE
<222> LOCATION: (29)..(29)
<223> OTHER INFORMATION: or Ser

```
<220> FEATURE:
<221> NAME/KEY: MISC_FEATURE
<222> LOCATION: (30)..(30)
<223> OTHER INFORMATION: or Ile
<220> FEATURE:
<221> NAME/KEY: MISC_FEATURE
<222> LOCATION: (31)..(31)
<223> OTHER INFORMATION: or His

<400> SEQUENCE: 34

Ile Xaa Ala Ile Xaa Leu Ala Xaa Pro Gly Ala Lys Xaa Gly Ile Leu
1               5                   10                  15

Met Xaa Ala Pro Leu Lys Xaa Ala Xaa Ala Gly Ala His Phe Gly
            20                  25                  30

<210> SEQ ID NO 35
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: DISULFID
<222> LOCATION: (12)..(17)
<220> FEATURE:
<221> NAME/KEY: MISC_FEATURE
<222> LOCATION: (19)..(21)
<223> OTHER INFORMATION: X is Dhb amino acid

<400> SEQUENCE: 35

Val Gly Ala Arg Tyr Leu Ala Xaa Pro Gly Ala Ala Trp Lys Leu Val
1               5                   10                  15

Ala Phe Xaa Xaa Xaa Val Lys
            20

<210> SEQ ID NO 36
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: DISULFID
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (13)..(18)
<220> FEATURE:
<221> NAME/KEY: MOD_RES
<222> LOCATION: (13)..(13)
<223> OTHER INFORMATION: Abu
<220> FEATURE:
```

```
<221> NAME/KEY: MOD_RES
<222> LOCATION: (18)..(18)
<223> OTHER INFORMATION: Abu
<220> FEATURE:
<221> NAME/KEY: 19DISULFID
<222> LOCATION: (19)..(22)
<220> FEATURE:
<221> NAME/KEY: 19DISULFID
<222> LOCATION: (25)..(29)
<220> FEATURE:
<221> NAME/KEY: MOD_RES
<222> LOCATION: (25)..(25)
<223> OTHER INFORMATION: Abu

<400> SEQUENCE: 36

Val Leu Ala Lys Xaa Leu Ala Xaa Pro Gly Ala Ile Xaa Gly Pro Leu
1               5                   10                  15

Gln Xaa Ala Trp Leu Ala Phe Pro Xaa Phe Ala Lys Ala
            20                  25

<210> SEQ ID NO 37
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: DISULFID
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (13)..(18)
<220> FEATURE:
<221> NAME/KEY: MOD_RES
<222> LOCATION: (13)..(13)
<223> OTHER INFORMATION: Abu
<220> FEATURE:
<221> NAME/KEY: MOD_RES
<222> LOCATION: (18)..(18)
<223> OTHER INFORMATION: Abu
<220> FEATURE:
<221> NAME/KEY: DISULFID
<222> LOCATION: (19)..(25)
<220> FEATURE:
<221> NAME/KEY: MISC_FEATURE
<222> LOCATION: (23)..(23)
<223> OTHER INFORMATION: X is Dhb amino acid
<220> FEATURE:
<221> NAME/KEY: MOD_RES
<222> LOCATION: (25)..(25)
<223> OTHER INFORMATION: Abu
<220> FEATURE:
<221> NAME/KEY: DISULFID
<222> LOCATION: (26)..(28)
<220> FEATURE:
<221> NAME/KEY: MISC_FEATURE
<222> LOCATION: (31)..(31)
<223> OTHER INFORMATION: X is Dha amino acid

<400> SEQUENCE: 37

Trp Lys Ala Glu Xaa Val Ala Xaa Pro Gly Ala Val Xaa Gly Val Leu
1               5                   10                  15

Gln Xaa Ala Phe Leu Gln Xaa Ile Xaa Ala Asn Ala His Ile Xaa Lys
            20                  25                  30
```

```
<210> SEQ ID NO 38
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: DISULFID
<222> LOCATION: (13)..(19)
<220> FEATURE:
<221> NAME/KEY: MOD_RES
<222> LOCATION: (13)..(13)
<223> OTHER INFORMATION: Abu
<220> FEATURE:
<221> NAME/KEY: MISC_FEATURE
<222> LOCATION: (18)..(18)
<223> OTHER INFORMATION: X is Dhb amino acid
<220> FEATURE:
<221> NAME/KEY: DISULFID
<222> LOCATION: (23)..(26)
<220> FEATURE:
<221> NAME/KEY: MOD_RES
<222> LOCATION: (23)..(23)
<223> OTHER INFORMATION: Abu
<220> FEATURE:
<221> NAME/KEY: MISC_FEATURE
<222> LOCATION: (29)..(29)
<223> OTHER INFORMATION: X is Dha amino acid

<400> SEQUENCE: 38

Trp Lys Ala Glu Xaa Leu Ala Xaa Pro Gly Ala Val Xaa Gly Ala Leu
1               5                   10                  15

Gln Xaa Ala Phe Leu Gln Xaa Ala Asn Ala Lys Ile Xaa Lys
            20                  25                  30

<210> SEQ ID NO 39
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: or V or I
<220> FEATURE:
<221> NAME/KEY: DISULFID
<222> LOCATION: (3)..(7)
<220> FEATURE:
<221> NAME/KEY: MISC_FEATURE
<222> LOCATION: (6)..(6)
<223> OTHER INFORMATION: or L
<220> FEATURE:
<221> NAME/KEY: DISULFID
<222> LOCATION: (8)..(11)
<220> FEATURE:
<221> NAME/KEY: MOD_RES
<222> LOCATION: (8)..(8)
<223> OTHER INFORMATION: Abu
```

```
<220> FEATURE:
<221> NAME/KEY: MISC_FEATURE
<222> LOCATION: (14)..(14)
<223> OTHER INFORMATION: X is Dha amino acid
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: lanthionine bridge

<400> SEQUENCE: 39

Ile Ala Ala Lys Phe Ile Ala Xaa Pro Gly Ala Ala Lys Xaa Gly Ala
1               5                   10                  15

Phe Asn Ala Tyr Ala
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MISC_FEATURE
<222> LOCATION: (6)..(6)
<223> OTHER INFORMATION: or Leu
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: MISC_FEATURE
<222> LOCATION: (13)..(13)
<223> OTHER INFORMATION: or Lys
<220> FEATURE:
<221> NAME/KEY: MISC_FEATURE
<222> LOCATION: (14)..(14)
<223> OTHER INFORMATION: X is Dhb amino acid
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: lanthionine bridge

<400> SEQUENCE: 40

Phe Lys Ala Trp Xaa Leu Ala Xaa Pro Gly Ala Ala Arg Xaa Gly Ala
1               5                   10                  15

Phe Asn Ala Tyr Ala
            20

<210> SEQ ID NO 41
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
```

```
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: DISULFID
<222> LOCATION: (8)..(11)
<220> FEATURE:
<221> NAME/KEY: DISULFID
<222> LOCATION: (18)..(23)
<220> FEATURE:
<221> NAME/KEY: MISC_FEATURE
<222> LOCATION: (21)..(23)
<223> OTHER INFORMATION: lanthionine bridge

<400> SEQUENCE: 41

Phe Xaa Ala Leu Xaa Leu Ala Ala Leu Gly Ala Thr Gly Val Lys Asn
1               5                   10                  15
Pro Ala Phe Asn Ala Tyr Ala
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (4)..(4)
<223> OTHER INFORMATION: W is 5-cholor-Trp
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: DISULFID
<222> LOCATION: (13)..(18)
<220> FEATURE:
<221> NAME/KEY: MOD_RES
<222> LOCATION: (14)..(14)
<223> OTHER INFORMATION: 4Hyp
<220> FEATURE:
<221> NAME/KEY: DISULFID
<222> LOCATION: (20)..(23)
<220> FEATURE:
<221> NAME/KEY: MISC_FEATURE
<222> LOCATION: (21)..(23)
<223> OTHER INFORMATION: lanthionine bridge

<400> SEQUENCE: 42

Val Xaa Ala Trp Xaa Leu Ala Xaa Pro Gly Ala Thr Ala Pro Gly Gly
1               5                   10                  15
Gly Ala Asn Ala Ala Phe Ala
            20
```

```
<210> SEQ ID NO 43
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Dhb amino acid
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: DISULFID
<222> LOCATION: (8)..(11)
<220> FEATURE:
<221> NAME/KEY: MOD_RES
<222> LOCATION: (8)..(8)
<223> OTHER INFORMATION: Abu
<220> FEATURE:
<221> NAME/KEY: MISC_FEATURE
<222> LOCATION: (14)..(14)
<223> OTHER INFORMATION: X is Dhb amino acid
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: lanthionine bridge

<400> SEQUENCE: 43

Phe Xaa Ala Val Xaa Phe Ala Xaa Pro Gly Ala Gly Glu Xaa Gly Ala
1               5                   10                  15

Phe Asn Ala Phe Ala
            20

<210> SEQ ID NO 44
<211> LENGTH: 22
<212> TYPE: PRT
<213> ORGANISM: Artificial Sequence
<220> FEATURE:
<223> OTHER INFORMATION: Mutant of Streptococcus mutans MU1140
<220> FEATURE:
<221> NAME/KEY: MOD_RES
<222> LOCATION: (1)..(1)
<223> OTHER INFORMATION: X stands for Phe, Ile, or Gly
<220> FEATURE:
<221> NAME/KEY: DISULFID
<222> LOCATION: (3)..(7)
<220> FEATURE:
<221> NAME/KEY: MOD_RES
<222> LOCATION: (4)..(4)
<223> OTHER INFORMATION: X stands for Trp, Ala, both Trp and Ala, or an
     absent amino acid
<220> FEATURE:
<221> NAME/KEY: MOD_RES
<222> LOCATION: (5)..(5)
<223> OTHER INFORMATION: X stands for Dha or Ala
<220> FEATURE:
<221> NAME/KEY: MOD_RES
<222> LOCATION: (8)..(8)
<223> OTHER INFORMATION: X stands for Abu or Ala
<220> FEATURE:
<221> NAME/KEY: DISULFID
<222> LOCATION: (8)..(11)
<220> FEATURE:
<221> NAME/KEY: MOD_RES
<222> LOCATION: (13)..(13)
<223> OTHER INFORMATION: X stands for Arg or Asp
```

```
<220> FEATURE:
<221> NAME/KEY: MOD_RES
<222> LOCATION: (14)..(14)
<223> OTHER INFORMATION: X stands for Dhb or Ala
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: Lanthionine bridge
<220> FEATURE:
<221> NAME/KEY: MOD_RES
<222> LOCATION: (22)..(22)
<223> OTHER INFORMATION: X stands for -CH=CH- or -CH2-CH2-

<400> SEQUENCE: 44

Xaa Lys Ala Xaa Xaa Leu Ala Xaa Pro Gly Ala Ala Xaa Xaa Gly Ala
1               5                  10                  15

Phe Asn Ala Tyr Ala Xaa
            20
```